US012748101B2

(12) United States Patent
Sanchez et al.

(10) Patent No.: US 12,748,101 B2
(45) Date of Patent: Sep. 29, 2026

(54) COMPOSITION AND METHOD FOR INHIBITING BORC COMPLEX TO TREAT CANCERS WITH NF1 DEFICIENCY AND DYSREGULATED RAS SIGNALING

(71) Applicant: THE TRUSTEES OF DARTMOUTH COLLEGE, Hanover, NH (US)

(72) Inventors: Yolanda Sanchez, Orford, NH (US); Stephanie Joy Bouley, North Smithfield, RI (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 543 days.

(21) Appl. No.: 17/641,877

(22) PCT Filed: Sep. 10, 2020

(86) PCT No.: PCT/US2020/050146

§ 371 (c)(1),
(2) Date: Mar. 10, 2022

(87) PCT Pub. No.: WO2021/050690

PCT Pub. Date: Mar. 18, 2021

(65) Prior Publication Data

US 2022/0326218 A1 Oct. 13, 2022

Related U.S. Application Data

(60) Provisional application No. 62/898,252, filed on Sep. 10, 2019.

(51) Int. Cl.

| | |
|---|---|
| ***A61P 35/00*** | (2006.01) |
| ***C12Q 1/02*** | (2006.01) |
| ***G01N 33/50*** | (2006.01) |

(52) U.S. Cl.

CPC .......... *G01N 33/5011* (2013.01); *A61P 35/00* (2018.01); *C12Q 1/025* (2013.01)

(58) Field of Classification Search

CPC ...... G01N 33/5011; C12Q 1/025; A61P 35/00
See application file for complete search history.

(56) References Cited

U.S. PATENT DOCUMENTS

| | | | |
|---|---|---|---|
| 2010/0209931 | A1 | 8/2010 | Sanchez et al. |
| 2013/0345268 | A1 | 12/2013 | Ratner et al. |

FOREIGN PATENT DOCUMENTS

| | | | |
|---|---|---|---|
| WO | WO 2017/059303 | A1 | 4/2017 |

OTHER PUBLICATIONS

Rosenbaum, T., and K. Wimmer. "Neurofibromatosis type 1 (NF1) and associated tumors." Klinische Pädiatrie (2014): 309-315. (Year: 2014).*

Luo, Jun, et al. "Modulation of the cellular distribution of human cytomegalovirus helicase by cellular factor Snapin." Journal of Virology 87.19 (2013): 10628-10640. (Year: 2013).*

Pu, Jing, et al. "BORC, a multisubunit complex that regulates lysosome positioning." Developmental cell 33.2 (2015): 176-188. (Year: 2015).*

International Patent Application No. PCT/US2020/050146 International Search Report and Written Opinion dated Feb. 8, 2021, 12 pages.

Allaway et al. "Exploiting mitochondrial and metabolic homeostasis as a vulnerability in NF1 deficient cells" Oncotarget, vol. 9, No. 22, 2018 pp. 15860-15875.

Pu et al. "BORC, a Multisubunit Complex that Regulates Lysosome Positioning" Dev Cell, 33(2), Apr. 20, 2015, 27 pages.

European Patent Application No. 20864091.2 extended European Search Report dated Sep. 1, 2023, 7 pages.

Langemeyer et al., "BORC and BLOC-1: Shared Subunits in Trafficking Complexes", Developmental Cell, 33, Apr. 20, 2015, 2 pages.

* cited by examiner

*Primary Examiner* — Kortney L. Klinkel
*Assistant Examiner* — Richard Grant Peckham
(74) *Attorney, Agent, or Firm* — Cozen O'Connor

(57) ABSTRACT

Disclosed herein are methods and compositions useful for identification of potential therapeutic agents for the treatment of a NF1- or RAS-associated disorder. Disclosed herein are also methods and compositions useful for the treatment of a NF1- or RAS-associated disorder.

3 Claims, 10 Drawing Sheets

Y102 az-Y102

Fig. 8A
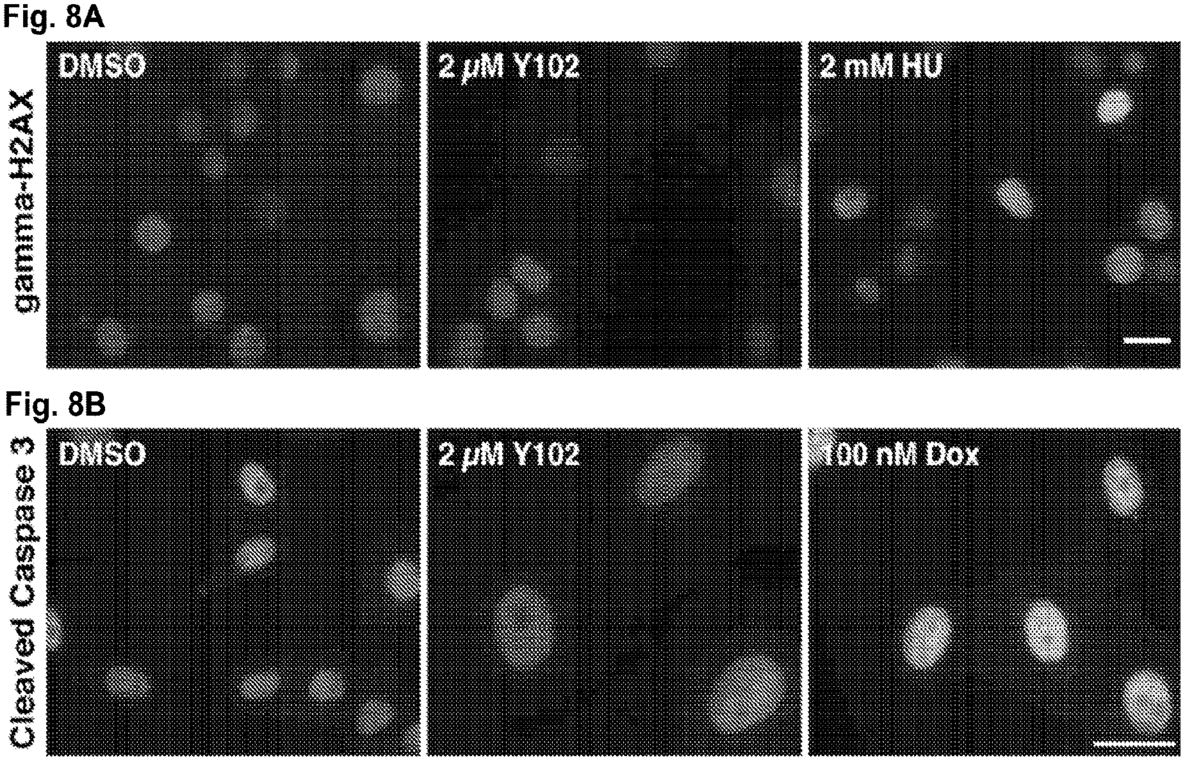
Fig. 8B
Fig. 8C
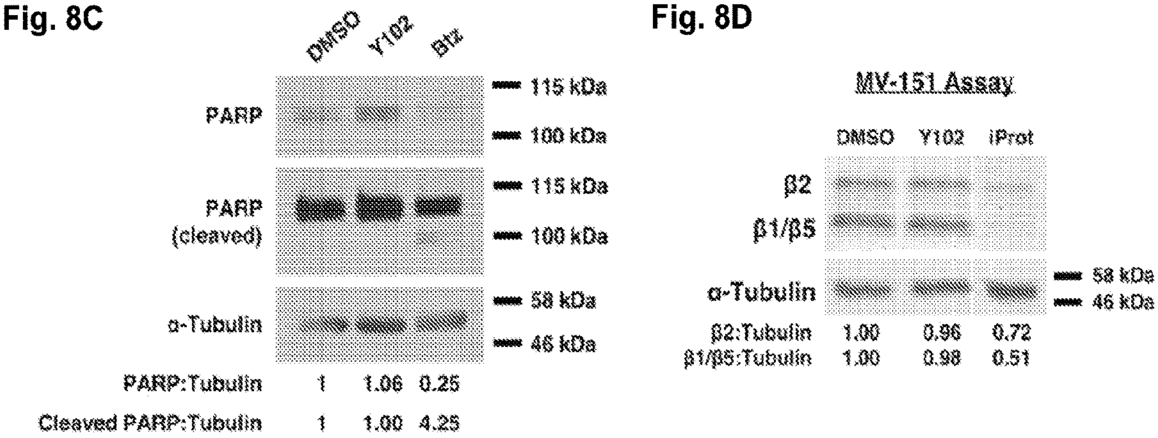
Fig. 8D

COMPOSITION AND METHOD FOR INHIBITING BORC COMPLEX TO TREAT CANCERS WITH NF1 DEFICIENCY AND DYSREGULATED RAS SIGNALING

CROSS-REFERENCE TO RELATED APPLICATIONS

This application claims benefit of priority to U.S. Provisional Patent Application No. 62/898,252 filed on Sep. 10, 2019, which is incorporated herein by reference in its entirety.

GOVERNMENT LICENSE RIGHTS

This invention was made with government support under grant numbers R01 NS095411 and R21 NS060940 awarded by the National Institutes of Health. The government has certain rights in the invention.

FIELD

The present invention relates to compositions and methods for treating disorders associated with NF1 and RAS, and to compositions and methods for screening for drug candidates for treating disorders associated with NF1 and RAS.

BACKGROUND

RASopathies are a group of rare genetic conditions defined by germline alterations in the RAS-MAPK pathway that often result in constitutive activation of the PI3K, RAF, and mTOR pathways located downstream of RAS (1). Together, these pathways drive translation, cell proliferation, cell motility, and cell invasion. One of the most common RASopathies with an incidence rate of 1:2,000-1:5,000 is neurofibromatosis type I (NF) (2). NF is an autosomal dominant tumor-predisposing syndrome categorized by the loss of neurofibromin (NF1) protein expression due to genetic mutation or other alterations in the NF1 gene. NF1 is a GTPase activating protein (GAP) that negatively regulates the activity of RAS by stimulating the intrinsic GTPase activity of RAS proteins; loss of NF1 results in RAS hyperactivation. RAS hyperactivation leads to the formation of non-malignant tumors including cutaneous neurofibromas (cNFs) and plexiform neurofibromas (PNs), in individuals with NF. cNFs are considered the largest tumor-related burden in NF patients, with no effective therapy options (3). Further, PNs can predispose individuals with NF to the development of malignant peripheral nerve sheath tumors (MPNSTs) (4, 5). MPNSTs are highly aggressive radiation- and chemotherapy-resistant tumors with a 5-year survival rate of 15-50% (6). NF patients can also develop a number of malignant tumor types including optic nerve gliomas, astrocytomas, juvenile myelomonocytic leukemia, and both low- and high-grade gliomas. Loss of NF1 also occurs in sporadic tumors including glioblastoma multiforme (GBM), breast cancer, ovarian cancer, melanoma, and lung cancer (7). Using genetically engineered mouse models NF1 loss has been shown to be a driver of GBM (8, 9). Currently there are no FDA-approved targeted therapies for patients diagnosed with a NF1-deficient benign PN, a MPNST, or NF1-deficient GBM (10). Over the past two decades, significant steps have been taken to address the lack of therapeutic options for those with NF1-deficient tumors, with a focus on targeting RAS effector proteins (11). Clinical trials focused on repurposing cancer drugs have been carried out in patients with PNs using RAF, mTOR, and MEK inhibitors (2). These inhibitors have had varying degrees of success; however, there are limitations associated with each of these inhibitors. RAF inhibitors such as dabrafinib are shown to be effective in BRAF-mutant melanomas; however, in BRAF-mutant melanomas with concurrent NF1 mutations RAF inhibitors are less effective due to remaining hyperactive RAS signaling (12). mTOR inhibitors are also effective in tumor types associated with RAS dysregulation; however, feedback signaling mediated by S6 kinase can increase AKT signaling, bypassing the inhibitory effects of the mTOR inhibitor (13). The combination of mTOR and PI3K inhibition is able to prevent this negative feedback loop but remains ineffective at inhibiting the RAF/MEK/ERK pathway (11). Work with MEK1/2 inhibitors such as selumetinib is encouraging and effective in the majority of NF participants with PNs or low-grade gliomas, and the drug was recently granted breakthrough therapy designation for the treatment of NF (14).

The instant disclosure uses an unbiased screening approach to identify novel targets for NF1-deficient tumors by developing a high-throughput synthetic lethal screen utilizing a library of tool compounds and a budding yeast model system of NF1 deficiency. Several promising compounds were discovered through this screen and the target or the mechanism of action of two of these were previously reported (15, 16). The instant disclosure provides the mechanism of action of a third compound, Y102, which identifies inhibition of lysosomal trafficking as a potential vulnerability of both sporadic and neurofibromatosis type I-associated NF1-deficient tumors.

The instant disclosure provides methods and platforms for identifying novel preclinical molecules and new therapeutic targets for treating conditions or disorders associated with NF1 or RAS.

SUMMARY

In an aspect, provided herein is a method of screening for compounds that inhibit a NF1 deficient cell, comprising the steps of (a) providing a compositing comprising a first cell comprising an alteration in ERG6 gene and an alteration in IRA2 gene, wherein the first cell further comprises a BORC complex or a conserved protein(s) that carries out the function of the BORC complex; (b) contacting the composition with a candidate compound; and (c) assaying a cellular characteristic known to be associated with an alteration in the BORC complex or the conserved protein(s) that carries out the function of the BORC complex in the first cell contacted with said candidate compound; wherein a candidate compound that affects the cellular characteristic indicates that the candidate compound is an inhibitor of a NF1 deficient cell.

In a second aspect, provided herein is a method for identifying a potential therapeutic agent for the treatment of a disorder associated with NF1 deficiency comprising the steps of (a) providing a composition comprising a cell comprising an alteration in ERG6 gene and an alteration in IRA2 gene, wherein the cell further comprises a BORC complex or a conserved protein(s) that carries out the function of the BORC complex; (b) contacting the composition with a candidate compound; and (c) assaying a cellular characteristic known to be associated with the alteration in the BORC complex or the conserved protein(s) that carries out the function of the BORC complex in the cell contacted with said candidate compound; wherein a candidate compound that affects said cellular characteristic is identified as a potential therapeutic agent for the treatment of a disorder associated with NF1 deficiency.

In a third aspect, provided herein is a method for identifying a potential therapeutic agent for the treatment of a disorder associated with NF1 deficiency comprising the steps of (a) providing a composition comprising a cell comprising an alteration in ERG6 gene and an alteration in IRA2 gene, wherein the cell further comprises a BORC complex or a conserved protein(s) that carries out the function of the BORC complex; (b) contacting the composition with a candidate compound; (c) assaying whether the candidate compound interacts with the BORC complex or the conserved protein(s) that carries out the function of the BORC complex in the cell; wherein a candidate compound that interacts with the BORC complex is identified as a potential therapeutic agent for the treatment of a disorder associated with NF1 deficiency.

In a fourth aspect, provided herein is a method for treating or reducing a risk of having a disorder associated with NF1 deficiency.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of the steps or features.

BRIEF DESCRIPTION OF THE FIGURES

The following figures form part of the present specification and are included to further illustrate aspects of the present invention.

(FIG. 1A) Schematic of screen design. The efficacy of compounds was compared between erg6Δ and erg6Δira2Δ yeast. Compounds were considered hits if erg6Δira2Δ yeast exhibited slow growth or death at concentrations that had no effect on the growth of erg6Δ yeast. (FIG. 1B) Chemical structure of small molecule Y102. (FIG. 1C) Yeast were grown at 30° C. starting at an OD600 of 0.05 with Y102 at concentrations ranging from 100 μM to 0.039 μM. At 18 h, OD600 was measured. Results are normalized to DMSO and are an average of three experiments. Error bars represent the standard deviation. (FIG. 1D) U87-MG cells were treated for up to 7 days with Y102 at concentrations ranging from 100 μM to 0.039 μM. Following treatment, cells were stained with 1 μg/mL Hoechst 33258 and absorbance was read at ex/em 355/460 nm. Error bars represent the standard deviation. (FIG. 1E) U251-MG cells were treated for up to 3 days with Y102 at concentrations ranging from 20 μM to 0.039 μM. Three hours prior to collection, cells were stained with alamarBlue. Plates were read at an ex 544 nm/em 590 nm. Error bars represent the standard deviation. (FIG. 1F) sNF96.2 cells were treated for up to 3 days with Y102 at concentrations ranging from 100 μM to 0.039 μM. Following treatment, cells were stained with 1 μg/mL Hoechst 33258 and absorbance was read at ex/em 355/460 nm. Error bars represent the standard deviation. (FIGS. 1G-1H) U87-MG cells were treated for up to 3 days with Y102 at concentrations ranging from 100 μM to 0.039 μM. Following treatment, cells were stained with 1 μg/mL Hoechst 33258 and absorbance was read at ex/em 355/460 nm. Error bars represent the standard deviation. (FIGS. 1D-1G) Results are normalized to DMSO. (FIG. 1H) Results are normalized to day zero plating.

(FIG. 2A) U87-MG cells were treated with DMSO, 2 μM Y102, or 50 μM HCQ, an autophagy inhibitor, for 24 hours. Cells were stained for the autophagy marker p62 (red). DAPI was used to counterstain cell nuclei (blue). Scale bar=50 μm (FIG. 2B) 100 cells were analyzed in triplicate experiments, and one-way ANOVA statistical analysis was performed. Error bars represent the standard deviation. (FIG. 2C) Western immunoblotting analysis of autophagy markers following 12 h treatment+/−12 h with HCQ. Densitometry analysis was used to determine the ratios of p62 and LC3-I/II to α-Tubulin control. (FIG. 2D) U87-MG cells were treated with DMSO, 2 μM Y102, or 50 μM HCQ for 24 hours. 30 minutes prior to the end of treatment, cells were stained with MitoTracker Red CMXROS (red). DAPI was used to counterstain cell nuclei (blue). Scale bar=50 μm (FIG. 2E) 100 cells were analyzed in triplicate experiments to determine differences in perinuclear clustering between treatment conditions. Statistical analysis was performed as in FIG. 2B. (FIG. 2F) U87-MG cells were treated with DMSO, 2 μM Y102, 50 μM HCQ, or 100 μM tBHP, an inducer of oxidative stress, for 24 hours. 30 minutes prior to collection, cells were stained with MitoTracker Red CMXROS (red). Cells were stained for oxidative stress marker 8-hydroxyguanosine (8-OHG) (green). DAPI was used to counterstain cell nuclei (blue). Scale bar=50 μm (FIG. 2G) Quantification of 8-OHG positive cells. 100 cells were analyzed in triplicate experiments. Statistical analysis was performed as in FIG. 2B. For one-way ANOVA: >0.1234 (NS), 0.0332 (*), 0.0021 (), 0.0002 (*), <0.0001 (****).

(FIG. 3A) U87-MG cells were treated for 24 h with DMSO, 2 μM Y102, or 100 μM CoCl2. 30 minutes prior to collection, cells were stained with MitoTracker Red CMXROS (red). Cells were also stained for the mitophagy receptor BNIP3L/Nix (green). DAPI was used to counterstain cell nuclei (blue). Scale bar=50 μm (FIG. 3B) Quantification of Nix expression. 100 cells were analyzed from triplicate experiments. Statistical analysis was performed as in FIG. 2B. (FIG. 3C) qPCR analysis of Nix mRNA expression following Y102 treatment compared to DMSO. (FIG. 3D) Western immunoblotting analysis of Nix expression after 2 h 20 μM QVD pre-treatment, followed by 24 h co-treatment with DMSO, 2 μM Y102, 100 μM CoCl2, or 10 μM CCCP. α-Tubulin served as a loading control. (FIG. 3E) U87-MG cells were treated for 16 h with DMSO, 2 μM Y102, 2 μM JW-1, 50 μM HCQ, or 100 μM CoCl2. Cells were stained for the lysosome marker LAMP1 (red) and the mitochondria marker Tom20 (green). DAPI was used to counterstain cell nuclei (blue). Ratiometric images comparing the colocalization between mitochondria and lysosomes were generated using Fiji. Resulting fluorescence is displayed as intensities (16-color; color bar on right). Scale bar=50 μm.

(FIG. 4A) Yeast were grown at 30° C. starting at an OD600 of 0.05 with Y102 or various analogs of Y102 at concentrations ranging from 100 μM to 0.039 μM. At 18 h, OD600 was measured. Error bars represent the standard deviation. (FIG. 4B) U87-MG cells were treated for 72 h with Y102 or various analogs of Y102 at concentrations ranging from 100 μM to 0.039 μM. Three hours prior to collection, cells were stained with alamarBlue. Plates were read at an ex 544 nm/em 590 nm. Error bars represent the standard deviation. (FIG. 4C) Chemical structure of azide-tagged Y102 (az-Y102), modification based on the structure-activity relationship studies performed with analogs of Y102. (FIG. 4D) Yeast were grown at 30° C. starting at an OD600 of 0.05 with Y102 or az-Y102 at concentrations ranging from 100 μM to 0.039 μM. At 18 h, OD600 was measured. Error bars represent the standard deviation. (FIG. 4E) U87-MG cells were treated for 72 h with Y102 or az-Y102 at concentrations ranging from 100 μM to 0.039 μM. Three hours prior to collection, cells were stained with alamarBlue. Plates were read at an ex 544 nm/em 590 nm. Error bars represent the standard deviation. (FIG. 4F) Comparison between the two proteomics approaches, along with the implementation of additional criteria to the results, led to the identification of two potential targets of Y102: p21 and the BORC complex. (FIG. 4G) CETSA results for p21 and BORCS6. Graphs represent triplicate analyses and measure the fraction of soluble protein following exposure to the indicated temperatures. (FIG. 4H) Click-chemistry enriched pulldown results for p21 and BORCS7. Graphs represent triplicate analyzes and measure the iBAQ area ratio between az-Y102 and parent compound Y102. α-Tubulin is included as a comparative control. Error bars represent the standard deviation.

(FIG. 5A) U87-MG cells were treated with negative (siNeg) or BORCS6-specific (siBORCS6) siRNA. following 72 h knockdown, cells were stained for the lysosome marker LAMP1 (red), the autophagy marker p62 (red), and the mitophagy receptor Nix (green). DAPI was used to counterstain cell nuclei (blue). Scale bar=150 μm (FIG. 5B) U87-MG cells were plated at 200,000 cells/well and treated for 72 h with siNeg or siBORCS6. 50 μg of lysate was run on a 4-15% SDS-PAGE gel, transferred to nitrocellulose, and probed for BORCS6. Densitometry analysis was used to determine the ratios of BORCS6 to α-Tubulin control to determine sufficient knockdown. Blot is representative of two experiments.

(FIG. 6C) 100 cells were analyzed to in triplicate experiments to determine the average nucleus size. Statistical analysis was performed as in FIG. 2B. (FIG. 6D) 100 cells were analyzed in triplicate experiments to determine the average nucleus size of p21-positive cells. n indicates number of positive cells out of 300 total cells. Statistical analysis was performed as in FIG. 2B. (FIG. 6E) U87-MG cells were treated for 24 h with DMSO, 2 μM Y102, or 100 μM CoCl2. Following treatment, cells were trypsinized, permeabilized, and stained with DAPI. Samples were analyzed on the MacsQuant VYB and 50,000 events were collected using the V1 channel. Data presented is the percent of cells in each stage of the cell cycle as measured by flow cytometry for duplicate experiments. Statistical analysis was performed as in FIG. 2B. (FIG. 6F) To measure senescence, U87-MG cells were treated for 72 h with DMSO, 2 μM Y102, or 100 nM Doxorubicin. Following treatment, cells were fixed and stained with 1 mg/mL β-galactosidase solution. 100 cells were analyzed in triplicate to determine the number of β-galactosidase positive cells. Statistical analysis was performed as in FIG. 2B. (FIG. 6G) U87-MG cells were treated with negative (siNeg) or BORCS6-specific (siBORCS6) siRNA. following 72 h knockdown, cells were stained for the cell cycle regulator p21 (green). DAPI was used to counterstain cell nuclei (blue). Scale bar=150 μm (FIG. 6H) Quantification of p21 positive cells. 100 cells were analyzed in triplicate experiments. Statistical analysis was performed as in FIG. 2B. (FIG. 6I) 100 cells were analyzed to determine the average nucleus size. Statistical analysis was performed as in FIG. 2B. (FIG. 6J) 100 cells were analyzed to determine the average nucleus size of p21-positive cells. Statistical analysis was performed as in FIG. 2B. For one-way ANOVA: >0.1234 (NS), 0.0332 (*), 0.0021 (), 0.0002 (*), <0.0001 (****).

(FIG. 7A) U87-MG cells containing an empty vector or expressing flag-tagged BORCS6 were treated with az-Y102, Y102, or DMSO. Following treatment, az-Y102 was labeled with alkyne-488 via click chemistry (green), and BORCS6 was visualized using anti-Flag (red). Nuclei are labeled in blue. Ratiometric images comparing the colocalization between mitochondria and lysosomes were generated using Fiji. Resulting fluorescence is displayed as intensities (16-color; color bar on right). Scale bar=50 μm (FIG. 7B) U87-MG cells or a clone expressing flag-tagged BORCS6 were plated at 200,000 cells/well. 50 μg of lysate was run on a 4-15% SDS-PAGE gel, transferred to nitrocellulose, and probed for BORCS6. Densitometry analysis was used to determine the ratios of BORCS6 to GAPDH control to determine sufficient knockdown. (FIG. 7C) Proposed mechanism of action for Y102. Y102 treatment prevents BORC-driven lysosomal trafficking from the perinuclear region to the cell periphery, resulting in the perinuclear clustering of lysosomes. Image made using Microsoft PowerPoint.

FIGS. 8A-8D: The mechanism of Y102-mediated cell death is not driven by apoptosis or proteasome inhibition. (FIG. 8A) U87-MG cells were treated for 24 h with DMSO, 2 μM Y102, or 2 mM Hydroxyurea. Cells were stained for γ-H2AX, a double- and single-stranded DNA breaks marker (green). DAPI was used to counterstain cell nuclei (blue). Scale bar=150 μm (FIG. 8B) U87-MG cells were treated for 48 h with DMSO, 2 μM Y102, or 100 nM Doxorubicin. Cells were stained for cleaved-caspase 3, an apoptotic cell death marker (green). DAPI was used to counterstain cell nuclei (blue). Scale bar=150 μm (FIG. 8C) (FIG. 8D) U87-MG cells were treated for 24 h with DMSO or 2 μM Y102, or for 2 h with a combination of 1 μM Bortezomib and 10 μM MG-132. Cell lysates were incubated with the dye MV-151, which binds to the active sites of proteasomal subunits. Samples were run on an SDS-PAGE gel. Fluorescence was measured by scanning the gel on a Typhoon scanner. Protein was transferred to nitrocellulose to probe for the loading control α-Tubulin. Densitometry analysis was used to determine the ratios of active proteosome subunits to α-Tubulin control. Experiment was repeated twice and the image is representative of both experiments.

(FIGS. 9A and 9C) Yeast were grown at 30° C. starting at an OD600 of 0.05 with Y102 or various analogs of Y102 at increasing concentrations starting from 100 μM. At 18 h, OD600 was measured. (FIGS. 9B and 9D) U87-MG cells were plated at 5,000 cells/well and treated for 72 h with Y102 or various analogs of Y102 at concentrations ranging from 100 μM to 0.039 μM. Three hours prior to collection, cells were stained with alamarBlue. Plate fluorescence was read at an ex/em of 544 nm/590 nm.

DETAILED DESCRIPTION

Figure 1A:
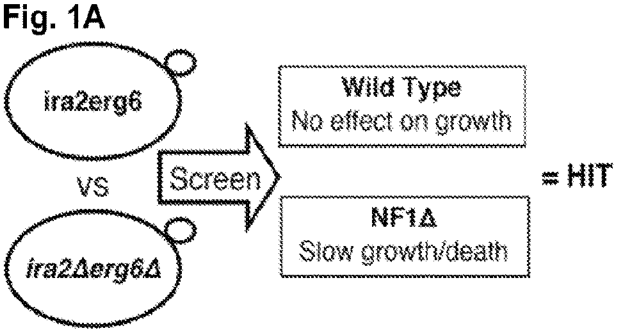
FIGS. 1A-1H: Y102 is synthetic lethal in NF1-deficient yeast and exhibits activity in NF1-deficient human tumor cell lines.

Disclosed herein are methods and compositions useful for identification of potential therapeutic agents for the treatment of a disorder associated with NF1 and RAS. Disclosed herein are also methods and compositions useful for the treatment of a disorder associated with NF1 and RAS.

Definitions

For convenience, before further description of the present invention, certain terms used in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art. The terms used throughout this specification are defined as follows, unless otherwise limited in specific instances.

The articles "a," "an" and "the" are used to refer to one or to more than one (i.e., to at least one) of the grammatical object of the article.

The term "alteration" as used herein is intended to encompass any mutation or deletion of a gene, including truncation, deletion of the entire sequence or a portion of the gene, or one or more mutations that result in ablated or significantly attenuated gene function, "loss of function," such that the net result of the alteration is to essentially or substantially reduce the function of a gene of interest such that the assay as described herein can be effectively carried out to identify potential therapeutic agents. The term may also encompass any mutation that results in suppression or altered translation or transcription of the gene of interest, such that the gene function is essentially or substantially reduced in function. Determination of alterations with respect to a particular gene that satisfies the above-definition may be determined via routine experimentation.

As used herein, "biologically acceptable medium" includes any and all solvents, dispersion media, and the like which may be appropriate for the desired route of administration of the pharmaceutical preparation. The use of such media for pharmaceutically active substances is known in the art.

The terms "candidate agent" or "candidate compound" or "candidate molecule" or "candidate drug" may be used interchangeably and encompass an agent, compound, or molecule which has the potential to have a therapeutic effect in vivo or in vitro which can be used with the disclosed methods to determine whether the agent or compound has a desired biological or biochemical activity.

The phrase "cellular characteristic associated with a proliferative disorder" as used herein is intended to include any feature or property, whether biological or biochemical, of a cell or cellular population that may be indicative of a proliferative disorder, particularly that of NF1 or an NF1 related disease. For example, the characteristic may be but is not limited to, migration, proliferation, rate of cell growth, cellular adhesion, inhibition of mitochondria clearance, inhibition of lysosome distribution, inhibition of BORC complex, or interaction with BORC complex. The cellular characteristic may be that of individual cells or a population of cells.

As used herein, "chemical library" or "compound library" generally refers to a collection of stored chemicals often used in high-throughput screening or industrial manufacture. The library may comprise a series of stored chemicals, each chemical typically having associated information stored in a database. The associated information may include, for example, the chemical structure, purity, quantity, and physiochemical characteristics of the compound. Chemical or compound libraries may focus on large groups of varied organic chemical series such that an organic chemist can make many variations on the same molecular scaffold or molecular backbone. Chemicals may also be purchased from outside vendors as well and included into an internal chemical library.

As used herein, the term "compound" (e.g., as in "candidate compound") includes both exogenously added candidate compounds and peptides endogenously expressed from a peptide library. For example, in certain aspects, the reagent cell may produce the candidate compound being screened. For instance, the reagent cell can produce. e.g., a candidate polypeptide, a candidate nucleic acid and/or a candidate carbohydrate which may be screened for its ability to modulate the receptor/channel activity. In such aspects, a culture of such reagent cells will collectively provide a library of potential effector molecules and those members of the library which either agonize or antagonize the receptor or ion channel function can be selected and identified. Moreover, it will be apparent that the reagent cell can be used to detect agents which transduce a signal via the receptor or channel of interest.

As used herein, the phrase "disorder associated with Ras deregulation or dysregulation" includes diseases wherein the etiology the disorder involves deregulation of RAS signaling, for example, wherein RAS activity may be increased to the extent that a disease state arises. The Ras forms contemplated herein encompass any known variant of Ras and include K-Ras (for example, NCBI Accession Number NG 007524) (having two splice variants), H-Ras (for example, NCBI Accession Number NG 007666), and N-Ras (for example, NCBI Accession Number NG 007572), and R-Ras (for example, NCBI Accession Number NC_000019 (Gene ID 6237), Ras 1, Ras 2 and combinations thereof. The disorder associated with Ras deregulation or dysregulation may be a proliferative disorder such as cancer. The disorder associated with Ras deregulation or dysregulation may be Neurofibromatosis Type 1; a disease state that results from a mutation or loss of function in the NF1 gene (See U520100209931); pancreatic cancer; colon cancer; lung cancer; neurofibromas, malignant peripheral nerve sheath tumors, optic gliomas, Schwannomas, gliomas, leukemias, pheochromocytomas, pancreatic adenocarcinoma (wherein greater than about 90% of tumors have activating mutations in K-Ras), and/or other sporadic cancers, and may also include non-tumor manifestations such as learning disorders or and fungal infections such as those involving the transformation of fungi to the invasive hyphal form. In one aspect, the disorder may comprise a disorder caused by *Candida albicans*.

The terms "drug," "pharmaceutically active agent," "bioactive agent," "therapeutic agent," and "active agent" may be used interchangeably and refer to a substance, such as a chemical compound or complex, that has a measurable beneficial physiological effect on the body, such as a therapeutic effect in treatment of a disease or disorder, when administered in an effective amount. When these terms are used, or when a particular active agent is specifically identified by name or category, it is understood that such recitation is intended to include the active agent per se, as well as pharmaceutically acceptable, pharmacologically active derivatives thereof, or compounds significantly related thereto, including without limitation, salts, pharmaceutically acceptable salts, N-oxides, prodrugs, active metabolites, isomers, fragments, analogs, solvates hydrates, radioisotopes, etc.

As used herein, the terms "include" and "including" are not intended to be limiting in scope.

As used herein, the phrase "loss of function" means an alteration that causes a decrease or the total loss of the activity of the encoded protein. In one aspect, the decrease in activity and/or function is about 30%, or about 40%, or about 50%, or about 60%, or about 70%, or about 80%, or about 90%, or greater than about 95%.

As used herein, the term "mutation" means an alteration in a DNA or protein sequence, either by site-directed or random mutagenesis. A mutated form of a protein encompasses point mutations as well as insertions, deletions, or rearrangements. A mutant is an organism containing a mutation.

As used herein, the phrase "NF1-related disorder or condition" includes any disease state or disorder or symptoms that results from, or may be associated with, a mutation, deletion, dysregulation or other such alteration of the NF1 gene. Such disorders include Neurofibromatosis Type I. Associated conditions include neurofibromas, malignant peripheral nerve sheath tumors, optic gliomas, Schwannomas, gliomas, leukemias, pheochromocytomas and non-tumor manifestations, including learning disorders.

As used herein, the phrase "disorder or condition associated with NF1 deficiency" refers to any disease state or disorder or symptoms that results from, or may be related with, loss of function of the NF1 gene. The phase "NF1 deficient cells" includes cells having NF1 mutation, and cells that do not have NF1 mutation but have lost NF1 protein expression due to other mechanisms including gene silencing, protein degradation or microRNA interference with translation. Examples of disorder or condition associated with NF1 deficiency include, but not limited to, Neurofibromatosis Type I, optic gliomas, astrocytomas, juvenile myelomonocytic leukemia, high-grade gliomas, malignant peripheral nerve sheath tumors (MPNSTs), glioblastoma (GBM), melanoma, breast, ovarian and lung cancers.

The term "pharmaceutically-acceptable carrier," as used herein, means one or more compatible solid or liquid filler diluents or encapsulating substances which are suitable for administration to a mammal.

The term "compatible", as used herein, means that the components of the composition are capable of being comingled with the subject compound, and with each other, in a manner such that there is no interaction which would substantially reduce the pharmaceutical efficacy of the composition under ordinary use situations. When liquid dose forms are used, it may be advantageous for the disclosed compounds to be soluble in the liquid. Pharmaceutically-acceptable carriers must, of course, be of sufficiently high purity and sufficiently low toxicity to render them suitable for administration to the mammal being treated.

As used herein, the phrase "pharmaceutically acceptable salt(s)" includes salts of acidic or basic groups that may be present in compounds identified using the methods of the present invention. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, may include sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety may form pharmaceutically or cosmetically acceptable salts with various amino acids, in addition to the acids mentioned above. Compounds that are acidic in nature are capable of forming base salts with various pharmacologically or cosmetically acceptable cations. Examples of such salts include alkali metal or alkaline earth metal salts and, particularly, calcium, magnesium, sodium lithium, zinc, potassium, and iron salts.

As used herein, the term "potential therapeutic agent" means any candidate compound that may be identified, using the disclosed methods, as having a potential beneficial or therapeutic effect on one or more disorders described herein. Potential therapeutic agents may be identified by their effect on the disclosed, such effect generally comprising inhibition of viability, growth, proliferation, or migration of test cells, although variations of the effect or additional effects that can be measured will be recognized by one of ordinary skill in the art and are included within the scope of the invention. Potential therapeutic agents, as used herein, are identified as having a desired effect in vitro, and are considered "hits" which may be subjected to further in vitro or in vivo evaluation to determine or optimize the therapeutic benefit, or, alternatively, may be used to identify derivative or analogous agents which may in turn be evaluated for an in vivo or in vitro therapeutic effect.

As used herein, the terms "prevent," "preventing" and "prevention" mean the prevention of the development, recurrence or onset of a disorder or one or more symptoms thereof resulting from the administration of one or more compounds identified in accordance the methods of the invention or the administration of a combination of such a compound and a known therapy for such a disorder.

As used herein, the term "*Saccharomyces*" means a genus in the kingdom of fungi that includes many species of yeast. Yeasts such as *Saccharomyces cerevisiae* are single-celled fungi that multiply by budding, or in some cases by division (fission), although some yeasts such as *Candida albicans* may grow as simple irregular filaments (mycelium). They may also reproduce sexually, forming asci which contain up to eight haploid ascospores. *Saccharomyces cerevisiae* is commonly known as "bakers yeast", "budding yeast", or "brewers yeast".

As used herein, the term "therapeutically effective amount" means that amount of a therapy (e.g., a therapeutic agent) sufficient to result in (i) the amelioration of one or more symptoms of a disorder, (ii) prevent advancement of a disorder, (iii) cause regression of a disorder, or (iv) to enhance or improve the therapeutic effect(s) of another therapy.

As used herein, the term "prophylactically effective amount" means the amount of a compound disclosed herein sufficient to prevent, delay onset, or reduce the risk of developing a disorder or condition described herein.

As used herein, the terms "therapy" and "therapies" mean any method, protocol and/or agent that can be used in the prevention, treatment, management, or amelioration of a disease or disorder or one or more symptoms thereof. Similarly, as used herein, the terms "treat," "treatment" and "treating" refer to the reduction or amelioration of the progression, severity and/or duration of a disorder or one or more symptoms thereof.

As used herein, the term "yeast" means a unicellular fungus. The precise classification is a field that uses the characteristics of the cell, ascospore and colony. Physiological characteristics are also used to identify species. Budding yeasts are true fungi of the phylum Ascomycetes, class Saccharomycetes (also called Hemiascomycetes). The true yeasts are separated into one main order Saccharomycetales. The term "yeast" includes not only yeast in a strictly taxonomic sense, i.e., unicellular organisms, but also yeast-like multicellular fungi or filamentous fungi.

Unless otherwise indicated, conventional techniques of molecular biology (including recombinant techniques), microbiology, cell biology and biochemistry, are used herein, which are well within the skill of the art.

It was recognized that a cell based system having certain genetic modifications can provide an effective means for identifying potential therapeutic agents for the treatment of various disease states, particularly those disease states that result from or are associated with deregulation or dysregulation of Ras expression (i.e., "Ras deregulation") or NF1. NF1 deficient cells include cells having NF1 mutation, and cells that do not have NF1 mutation but have lost NF1 protein expression due to other mechanisms including gene silencing, protein degradation or microRNA interference with translation. Disease resulted from or associated with deregulation or dysregulation of Ras expression (i.e., "Ras deregulation") or NF1 may include, for example, Neurofibromatosis type 1 or other disorders associated with a mutation or loss of function in the NF1 gene (See US2010/0209931); various types of cancer; and/or disease states associated with fungal pathogenesis, particularly those wherein virulence is dependent upon Ras activation such as infection by *Candida albicans*. It is believed that the disclosed compositions and methods provide long awaited advantages over a wide variety of standard screening methods used for distinguishing and evaluating the efficacy of a compound in regulation of gene expression in a variety of disease states including those associated with fungal pathogens. For example, the methods allow for the identification, by genetic selection in a high throughput format, of peptides and compounds that specifically activate or inhibit, for example, fungal infection. These methods also allow the mode of action for such agents to be rapidly delineated. Moreover, these methods are amenable to an iterative compound modification and retesting process to allow for the evolution of more effective compounds from initial hits and leads.

Compositions

A composition comprising a test cell comprising an alteration in an IRA2 (See US2010/0209931) gene and an alteration in an ERG6 (See US2010/0209931) gene is used. In one embodiment, the test cell may comprise an alteration of both ERG6 and IRA2 ("erg6Δ ira2Δ strain"). Deletion of the ERG6 gene increases the permeability of ira2Δ cells to small molecules. Accordingly, the presence of an ERG6 functional deletion may be used to increase the sensitivity of the disclosed methods. Suitable cells and suitable strains may be obtained as described in detail in US2010/0209931.

Methods

It is believed that deletion of the yeast NF1 homologue IRA2 allows for an improved means for the discovery of small molecules that have different effects on the growth of drug-permeable strains by comparing the growth inhibition of erg6Δ ira2Δ to erg6Δ alone.

In an aspect, provided herein is a method of screening for compounds that inhibit a RAS deregulated or dysregulated cell, comprising the steps of (a) providing a composition comprising a first cell comprising an alteration in ERG6 gene and an alteration in IRA2 gene, wherein the first cell further comprises a BORC complex; (b) contacting the composition with a candidate compound; and (c) assaying a cellular characteristic known to be associated with an alteration in the BORC complex in the first cell contacted with said candidate compound; wherein a candidate compound that affects the cellular characteristic indicates that the candidate compound is an inhibitor of a RAS deregulated or dysregulated cell.

In one embodiment, the cellular characteristic is mitochondrial clearance, and wherein an inhibition of mitochondrial clearance indicates that the candidate compound is an inhibitor of a RAS deregulated or dysregulated cell. In another embodiment, the RAS deregulated or dysregulated cell is NF1 deficient. NF1 deficient cells include cells having NF1 mutation, and cells that do not have NF1 mutation but have lost NF1 protein expression due to other mechanisms including gene silencing, protein degradation or microRNA interference with translation. In another embodiment, the first cell is a yeast cell selected from the group consisting of *Saccharomyces cerevisiae, Candida albicans*, and *Aspergillus nidulans*. In another embodiment, the first cell is *Saccharomyces cerevisiae.*

In a second aspect, provided herein is a method for identifying a potential therapeutic agent for the treatment of a condition or disorder associated with RAS deregulation or dysregulation comprising the steps of (a) providing a composition comprising a cell comprising an alteration in ERG6 gene and an alteration in IRA2 gene, wherein the cell further comprises a BORC complex or a conserved protein(s) that carries out the function of the BORC complex; (b) contacting the composition with a candidate compound; (c) assaying a cellular characteristic known to be associated with the alteration in the BORC complex or the conserved protein(s) that carries out the function of the BORC complex in the cell contacted with said candidate compound; wherein a candidate compound that affects said cellular characteristic is identified as a potential therapeutic agent for the treatment of a disorder associated with RAS deregulation or dysregulation.

In one embodiment, the conserved protein that carries out the function of the BORC complex is BLOC-1.

In one embodiment, the cell is a yeast cell. In another embodiment, the cell is *Saccharomyces cerevisiae*. In another embodiment, the disorder associated with RAS deregulation or dysregulation is related with NF1. In another embodiment, the disorder is associated with NF1 deficiency. In another embodiment, the disorder is Neurofibromatosis Type 1.

In one embodiment, the disorder is neuroblastoma, lung adenocarcinoma, squamous cell carcinoma, glioblastoma, pancreatic cancer, ovarian cancer, colon cancer, lung cancer, neurofibromas, malignant peripheral nerve, sheath tumor, optic glioma, Schwannoma, glioma, leukemia, pheochromocytoma or pancreatic adenocarcinoma. In another embodiment, the disorder is neuroblastoma or glioblastoma. In another embodiment, the disorder is glioblastoma, melanoma, breast, ovarian, or long cancers.

In one embodiment, the cellular characteristic is lysosome-directed mitochondria clearance. In another embodiment, the cellular characteristic is mitochondrial clearance, and wherein an inhibition of mitochondrial clearance indicates that the compound is a potential therapeutic agent for the treatment of a disorder associated with NF1 deficiency.

In a third aspect, provided herein is a method for identifying a potential therapeutic agent for the treatment of a disorder associated with RAS deregulation or dysregulation comprising the steps of (a) providing a composition comprising a cell comprising an alteration in ERG6 gene and an alteration in IRA2 gene, wherein the cell further comprises a BORC complex or a conserved protein(s) that carries out the function of the BORC complex; (b) contacting the composition with a candidate compound; (c) assaying whether the candidate compound interacts with the BORC complex or the conserved protein(s) that carries out the function of the BORC complex in the cell; wherein a candidate compound that interacts with the BORC complex is identified as a potential therapeutic agent for the treatment of a disorder associated with RAS deregulation or dysregulation. In one embodiment, the disorder is related to NF1. In another embodiment, the disorder is associated with NF1 deficiency.

In one embodiment, the BORC complex comprises a plurality of subunits, and assaying whether the candidate compound interacts with the BORC complex comprising assaying whether the candidate compound interacts with at least one of the plurality of the subunits. In one embodiment, the at least one of the plurality of the subunits is BORCS6.

In a fourth aspect, provided herein a method for treating a disorder associated with RAS deregulation or dysregulation. In one embodiment, the method comprises administering a subject a compound that inhibits or interacts with a BORC complex. In another embodiment, the method comprises administering a subject comprising a compound that inhibits or interacts with a BORC complex and a pharmaceutically-acceptable carrier. In another embodiment, the method comprises administering a subject comprising a compound that inhibits or interacts with a BORC complex and a pharmaceutically-compatible adjuvant. In another embodiment, the method comprises administering a subject a therapeutically effective amount of a compound listed in Table 1 or pharmaceutically acceptable salts thereof. In one embodiment, the method comprises administering to a subject a therapeutically effective amount of an inhibitor of mitochondrial clearance. In another embodiment, the method comprises administering to a subject an inhibitor of lysosome distribution.

TABLE 1

| | |
|---|---|
| Y102 | 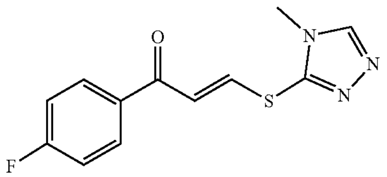 [SMILES: Cn1cnnc1S/C=C/C(=O)c1ccc(F)cc1] |
| JW-1 | 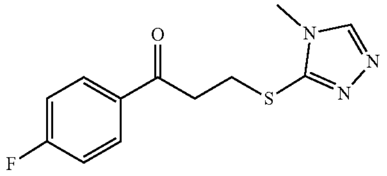 [SMILES: Cn1cnnc1SCCC(=O)c1ccc(F)cc1] |

TABLE 1-continued

| | |
|---|---|
| Y102_01 | 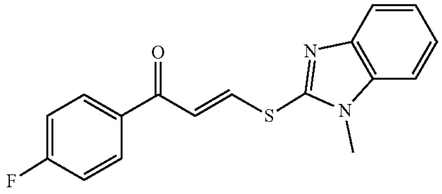 [SMILES: Cn1c(S/C=C/C(=O)c2ccc(F)cc2)nc2ccccc21] |
| Y102_02 | 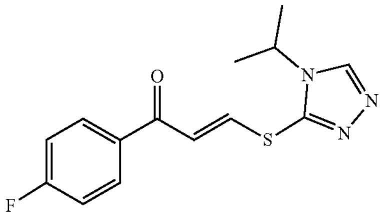 [SMILES: CC(C)n1cnnc1S/C=C/C(=O)c1ccc(F)cc1] |
| Y102_08 | 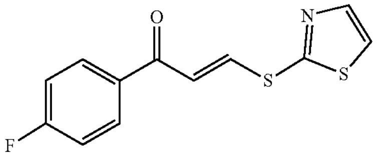 [SMILES: O=C(/C=C/Sc1nccs1)c1ccc(F)cc1] |
| Y102_17 | 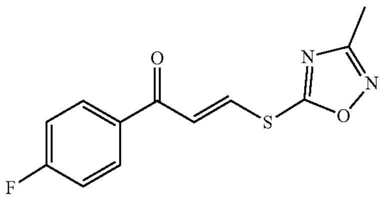 [SMILES: Cc1noc(S/C=C/C(=O)c2ccc(F)cc2)n1] |
| Y102_26 | 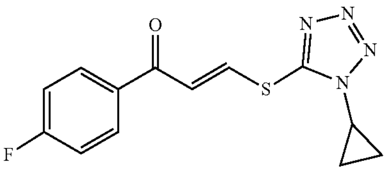 [SMILES: O=C(/C=C/Sc1nnnn1C1CC1)c1ccc(F)cc1] |
| Y102_29 | 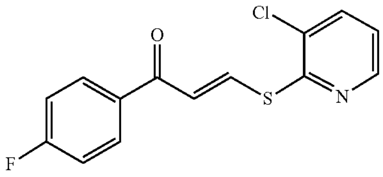 [SMILES: O=C(/C=C/Sc1ncccc1Cl)c1ccc(F)cc1] |
| Y102_30 | 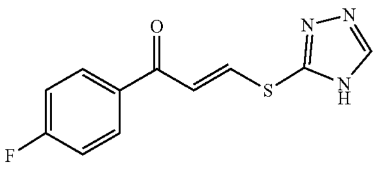 [SMILES: O=C(/C=C/Sc1nnc[nH]1)c1ccc(F)cc1] |
| Y102_31 | 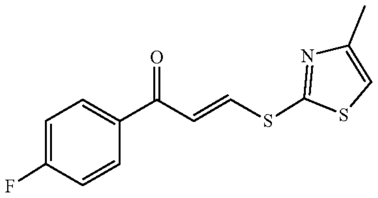 [SMILES: Cc1csc(S/C=C/C(=O)c2ccc(F)cc2)n1] |

TABLE 1-continued

| | |
|---|---|
| Y102_33 | 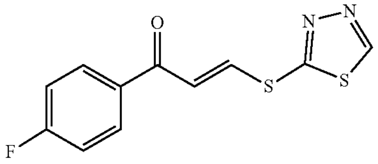 [SMILES: O=C(/C=C/Sc1nncs1)c1ccc(F)cc1] |
| Y102_35 | 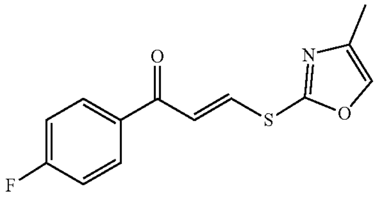 [SMILES: Cc1coc(S/C=C/C(=O)c2ccc(F)cc2)n1] |
| Y102_37 | 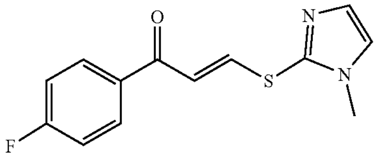 [SMILES: Cn1ccnc1S/C=C/C(=O)c1ccc(F)cc1] |
| Y102_43 | 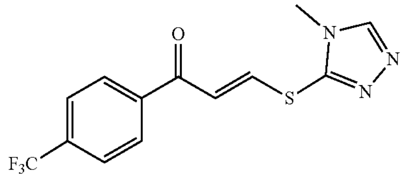 [SMILES: Cn1cnnc1S/C=C/C(=O)c1ccc(C(F)(F)F)cc1] |
| Y102_52 | 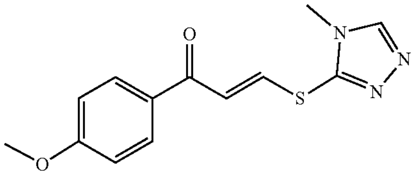 [SMILES: COc1ccc(C(=O)/C=C/Sc2nncn2C)cc1] |
| Y102_53 | 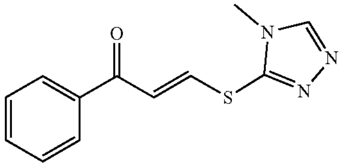 [SMILES: Cn1cnnc1S/C=C/C(=O)c1ccccc1] |
| Y102_55 | 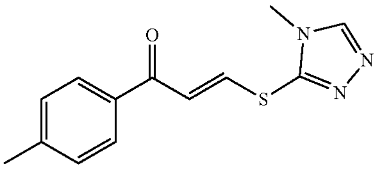 [SMILES: Cc1ccc(C(=O)/C=C/Sc2nncn2C)cc1] |
| Y102_58 | 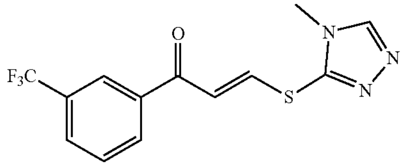 [SMILES: Cn1cnnc1S/C=C/C(=O)c1cccc(C(F)(F)F)c1] |
| Y102_60 | 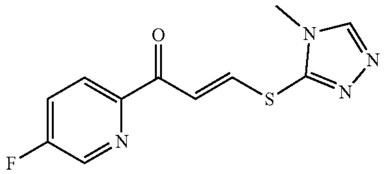 [SMILES: Cn1cnnc1S/C=C/C(=O)c1ccc(F)cn1] |

TABLE 1-continued

| | |
|---|---|
| Y102_A | 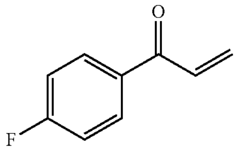 |
| Y102_B | 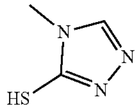 |

In one embodiment, the method disclosed involves the step of administering to a subject in need of treatment, e.g., a mammal (preferably a human) a prophylactically or therapeutically effective amount of one or more compound of Table 1. Subjects in need of treatment include those having, suspected of having, or at risk of having a disorder or condition associated with Ras deregulation or dysregulation and/or a NF1-related disorder or condition. A subject having or suspected of having a disorder or condition is one exhibiting one or more signs or symptoms associated with the disorder or condition. A subject at risk of having a disorder or condition includes, e.g., subjects having a mutation associated with the disorder or condition, but not showing signs or symptoms of the disorder or condition.

In one embodiment, the present disclosure provides methods for treating a disorder associated with NF1 deficiency comprising administering to a subject a therapeutically effective amount of a compound that interacts with a BORC complex.

In another embodiment, the present disclosure provides methods for preventing or reducing a risk of having a disorder associated with NF1 deficiency comprising administering to a subject a prophylactically effective amount of a compound that interacts with a BORC complex. In one embodiment, the compound is selected from the group consisting of compounds in Table 1.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of the steps or features.

Although the subject matter has been described in considerable detail with reference to certain embodiments thereof, other embodiments are possible. As such, the spirit and scope of the appended claims should not be limited to the description of the specific embodiments contained therein.

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

EXAMPLES

The disclosure will now be illustrated with working examples, and which is intended to illustrate the working of disclosure and not intended to restrictively any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Materials and Methods

Reagents

Y102 was originally purchased from Maybridge (NRB04162SC). Subsequent stocks of Y102, along with JW-1, all Y102 analogs, and the azide-tagged form of Y102 were synthesized by Enamine (Kiev, Ukraine). Bortezomib (Bz; S1013), MG-132 (S2619), and Rapamycin (S1039) were purchased from Selleckchem. Hydroxychloroquine Sulfate (HCQ; H1126) was purchased from Spectrum Chemical. tert-Butyl hydroperoxide solution (tBHP; 458139), Carbonyl cyanide 3-chlorophenylhydrazone (CCCP; C2759), and hydroxyurea (HU; H8627) were purchased from Sigma-Aldrich. Staurosporine (STS; S-9300) was purchased from LC Laboratories. Cobalt (II) Chloride (CoCl2; 36554) was purchased from Alfa Aesar. Stock solutions of compounds were prepared in 100% DMSO (Alfa Aesar) with the exception of HCQ and $CoCl_2$, which were prepared fresh in DMEM medium+10% FBS.

Cell Culture

U87-MG, U251-MG, and sNF96.2 cells were purchased from ATCC. U87-MG and U251-MG cell lines were cultured in DMEM with L-glutamine, 4.5 g/L glucose, and sodium pyruvate (Corning Life Sciences) with the addition of 10% v/v fetal bovine serum (FBS) (Atlanta Biologicals, Life Technologies). sNF96.2 cells were cultured in DMEM with 4 mM L-glutamine, 4.5 g/L glucose, 1 mM sodium pyruvate, and 1.5 g/L sodium bicarbonate (ATCC) with the addition of 10% v/v FBS. All cell lines were grown at 37° C. in 5% $CO_2$, passaged regularly using PBS and 0.25% trypsin (Corning), and routinely screened for mycoplasma using the MycoProbe Kit (R&D Systems).

A recent publication suggests that the current U87-MG cell line purchasable from ATCC differs from those of the original tumor; however, the cell line is considered to be a human glioblastoma cell line of unknown origin (19). In the context of this work, U87-MG cells serve as an NF1-deficient tumor cell line model, due to elevated proteasome-mediated degradation of the NF1 protein which is required for the establishment of tumors in xenograft mouse models (9). Various publications utilize U87-MG cells as a model of NF1-deficient tumor cell line (9, 11, 16, 46, 47).

Yeast Dose Response Curves

*S. cerevisiae* strains were plated at an OD600 of 0.05 in 96-well plates (Falcon) and treated with SC complete containing compound starting at 100 μM, followed by 2-fold serial dilutions to generate a 10-point range of concentrations normalized with DMSO; one row was treated with DMSO as a control. Yeast were incubated for 18 h. To process, the optical density was read using a Spectramax M2 (Molecular Devices) at a wavelength of 600 nm and normalized to DMSO. Each experiment was repeated 2-3 times with 4 technical replicates per experiment.

Hoechst Cell Death Viability Assays

Cells were plated at 2,500 cells/well in 96-well plates and allowed to adhere overnight. Medium was removed and replaced with media containing compound starting at 100 μM, followed by 2-fold serial dilutions to generate a 10-point range of concentrations normalized with DMSO; one row was treated with DMSO as a control. Cells were incubated for the indicated timepoints. Upon collection, media was removed, cells were rinsed with PBS, and stored at −80° C. until all plates were collected. To process cells, plates were thawed with PBS, incubated with 1× saline-sodium citrate (SSC) buffer with 0.02% sodium dodecyl sulfate (SDS) for 1 hour at 37° C., followed by staining with 1 μg/mL Hoechst 33258 (Pierce). Absorbance was read using a Spectramax M2 at an excitation of 355 nm and an emission of 460 nm, and absorbance was normalized to DMSO. Each experiment was repeated 2-3 times with 4 technical replicates per experiment.

alamarBlue Assays

Cells were plated at 5,000 cells/well in 96-well plates and allowed to adhere overnight. Medium was removed and replaced with media containing compound starting at 100 μM, followed by 2-fold serial dilutions to generate a 10-point range of concentrations normalized with DMSO; one row was treated with DMSO as a control. Cells were incubated for 72 h. 3 h prior to end of incubation, alamarBlue (Invitrogen) was added to a final concentration of 5% v/v. Fluorescence was read using a Spectramax M2 at an excitation of 544 nm and an emission of 590 nm, and fluorescence was normalized to DMSO. Each experiment contains 4 technical replicates.

Immunofluorescence Staining

U87-MG cells were plated at a concentration of 50,000 cells/well onto precoated poly-D-lysine (PDL) coverslips (Neuvitro) in 24-well plates (Falcon) and allowed to adhere overnight. Medium was removed and replaced with treatment-laced media normalized to DMSO, and cells were treated for the indicated timepoints. At the time of collection, cells were washed with PBS and fixed with 4% paraformaldehyde without methanol (EMS) or 100% methanol (Fischer). Coverslips were washed with Tween20-containing PBS (PBST; Fischer). Following permeabilization with 0.5% Triton X-100 in PBS (Fischer), coverslips were blocked for 1 h at room temperature in IF Buffer (0.05% azide, 0.2% Triton X-100, 2% Normal Goat Serum or, for 8-OHG, Normal Donkey Serum). The following primary antibodies were used for 1 hour at room temperature unless specified: AlexaFluor 488 pre-conjugated anti-γ-H2AX (N1-431) mouse monoclonal (30 minutes; BD Biosciences), anti-cleaved caspase 3 (Asp175) rabbit polyclonal (Cell Signaling), anti-SQSTM1/p62 (D-3) mouse monoclonal (Santa Cruz), anti-8-Hydroxyguanosine goat polyclonal (1:200; Millipore), anti-LAMP1 (D4O1S) mouse monoclonal (O/N at 4° C.; Cell Signaling), anti-BNIP3L/Nix (D4R4B) rabbit monoclonal (O/N at 4° C.; Cell Signaling), anti-FLAG (M2) mouse monoclonal (2 hours at 37° C.; Sigma-Aldrich). Following washes with PBST, cells were stained with goat anti-rabbit or goat anti-mouse AlexaFluor 488 or AlexaFluor 594 (or, for 8-OHG, donkey anti-goat AlexaFluor 488) secondary antibody at 1:800 for 1 hour at room temperature (Jackson ImmunoResearch). Coverslips were washed with PBST following secondary staining, cells were stained with 0.33 μg/mL DAPI in PBS and mounted onto slides in ProLong Gold (Life Technologies).

For MitoTracker Red CMXRos staining, 30 minutes prior to collection medium was removed and replaced with medium containing MitoTracker Red CMXRos at a final concentration of 100 nM (Molecular Probes). Following staining, cells were washed with PBS and fixed with 4% paraformaldehyde without methanol. Cells were washed with PBST, then permeabilized with 0.5% Triton X-100 in PBS. When co-staining with another marker, the staining procedure continued with the blocking step; otherwise, cells were stained with 0.33 μg/mL DAPI in PBS and mounted onto slides in ProLong Gold (Life Technologies).

To visualize the localization of az-Y102 using immunofluorescence, cells were treated for 2 hours with az-Y102, DMSO, or parent compound Y102, medium was removed and replaced with normal medium, and incubated for a total of 24 hours. Following treatment, cells were washed, fixed with 4% paraformaldehyde without methanol (EMS), and permeabilized using 0.5% Triton X-100 in PBS. Samples were stained with alkyne-488 at a final concentration of 1 μM following the Click-iT cell reaction buffer kit (Invitrogen) protocol. Following washes with 2% BSA, the staining procedure continued with the blocking step as described above.

All confocal images were acquired on a Nikon AIRSi confocal microscope equipped with a 60× 1.4 NA oil objective, a DU4 detector unit, and Nikon Elements software. Otherwise, images were acquired on a Zeiss Axio Imager.Z1 equipped with a Zeiss EC Plan-NEOFLUAR 40× 1.3 NA oil objective, a Zeiss AxioCam MRm camera, a Lumen Dynamics Series 120 Q X-Cite Fluorescence Illuminator, and AxioVision SE64 Rel. 4.9.1 software. Image processing was performed with Fiji, built on ImageJ2.

MV-151 Proteasome Active Site Inhibition Assay

U87-MG cells were plated at 500,000 cells/well in 6-well plates and allowed to adhere overnight (Falcon). Medium was removed and replaced with fresh medium containing Y102 or vehicle DMSO and treated for 24 h. As a positive control, one well was treated for 2 h with 1 μM Bz/10 μM MG-132.

Cells were collected after treatment by washing with PBS, harvested with trypsin plus agitation to detach cells, spun down in a centrifuge, and resuspended in PBS to wash. Cells were transferred to 1.5 mL microcentrifuge tubes, pelleted, and resuspended in 20 μL digitonin lysis buffer (50 mM Tris HCl pH 7.5, 250 mM sucrose, 2 mM EDTA, 1 mM ATP, 1 mM DTT, and 0.05% digitonin). Cells were mixed by pipetting, incubated on ice for 20 minutes, and the lysate was cleared by centrifugation. Protein concentrations were determined using a Bradford protein assay (Bio-Rad). 10 μg of protein lysate was incubated for 20 minutes with 20 μM MV-151 in a 37° C. water bath. 4× loading dye was added to the samples and proteins were separated by sodium dodecyl sulfate-polyacrylamide gel electrophoresis (SDS-PAGE) on a 4-15% polyacrylamide gradient gel (Bio-Rad). Gel was imaged on a Typhoon scanner at an excitation of 532 nm and an emission of 560 nm to detect MV-151 fluorescence. Following imaging, proteins were transferred to nitrocellulose. The blot was probed for α-Tubulin as a loading control. Experiment was repeated twice; shown is a representative image.

Western Immunoblotting

U87-MG cells were plated at 500,000 cells/well in 6-well plates and allowed to adhere overnight (Falcon). Medium was removed and replaced with fresh medium containing drugs or compounds for the indicated timepoints. Cells were collected after treatment by washing with PBS, harvested with trypsin plus agitation to detach cells, pelleted in a centrifuge and resuspended in PBS to wash. Cells were transferred to 1.5 mL microcentrifuge tubes, pelleted, and resuspended in RIPA lysis buffer (50 mM Tris pH 8.0, 150 mM NaCl, 1% nonidet P40, 0.5% sodium deoxycholate, and 0.05% SDS) containing 1 mM NaVO4, 1 mM NaF, 1 mM phenylmethylsulfonyl fluoride, 0.1 μg/mL antipain, 1 μM aprotinin, 100 μM benzamidine HCl, 0.1 μg/mL leupeptin, 0.1 μg/mL pepstatin, and 0.1 μg/mL soybean trypsin inhibitor. Protein was quantified using a BCA assay kit (Pierce). 50 μg of protein was prepared in 1× Laemmli sample buffer (50 mM Tris pH 6.8, 0.02% w/v bromophenol blue, 2% w/v SDS, 10% v/v glycerol, 1% v/v beta-mercaptoethanol, 12.5 mM EDTA) and separated by SDS-PAGE on a 4-15% polyacrylamide gradient gel (Bio-Rad). Protein was transferred to a nitrocellulose membrane, blocked with 5% nonfat dry milk in TBST and probed with anti-PARP (46D11) rabbit monoclonal (Cell Signaling, 1:5000, O/N at 4° C.), anti-BNIP3L/Nix (D4R4B) rabbit monoclonal (Cell Signaling, 1:1000, O/N at 4° C.), anti-p62/SQSTM-1 D-3 (Santa Cruz, 1:1000, 1 h at RT), anti-LC3BI/II #2775 (Cell Signaling, 1:1000, O/N at 4° C.), anti-C17orf59/BORCS6 rabbit polyclonal (Invitrogen, 1:1000, O/N at 4° C.), anti-GAPDH (14C10) rabbit monoclonal (Cell Signaling, 1:2500, 1 h at RT), or anti-alpha-tubulin (B-1-2-5) mouse (Santa Cruz, 1:10000, 1 h at RT) in 2% milk in TBST. Secondary labeling was performed with a one-hour incubation in 1:10000 anti-rabbit HRP or anti-mouse HRP (Jackson Immunoresearch) diluted in 2% milk in TBST. The film was exposed to ECL-coated blots (Pierce) and developed using a standard film processor.

Flow Cytometry

U87-MG cells were plated at 500,000 cells/well in a 6-well plate and allowed to adhere overnight. The medium was replaced with cell culture media containing DMSO, 2 μM Y102, 100 nM Doxorubicin, or 100 μM CoCl2 for 24 hours. At the end of the incubation, cells were rinsed twice with PBS, trypsinized, and rinsed again with PBS prior to fixation with BD cytofix/cytoperm for 30 minutes on ice. After washing with BD perm/wash twice, cells were stained with DAPI at a final concentration 0.33 μg/mL in PBS for 30 minutes on ice. Cells were washed twice more with BD perm/wash, and resuspended in PBS for analysis. The cells were transferred to flow cytometry tubes (14-961-10, Fisherbrand) and analyzed using a MacsQuant VYB 8-color flow cytometer. DNA content was detected using the V1 channel. This experiment was repeated twice, and the percentage of cells in each cell cycle stage is shown. 50,000 events per sample were collected and cellular debris was gated out of the dataset.

β-Galactosidase Senescence Assay

U87-MG cells were plated at 100,000 cells/well and allowed to adhere overnight. Medium was removed and replaced with medium containing DMSO, 2 μM Y102, or 100 nM Doxorubicin for a total of 72 hours. Cells were collected and stained for β-galactosidase using the Senescence β-Galactosidase Staining Kit (Cell Signaling). 100 cells were counted per condition; graph represents results from triplicate experiments.

Cellular Thermal Shift Assay and TMT 10-Plex labeling

U87-MG cells were plated into two 10 cm tissue culture dishes at a concentration that would result in a yield of approximately 1.5 mg total protein per plate on the day of collection. Cells were treated with 2 μM Y102, 2 μM JW-1, or DMSO for 2 hours. Media was removed and collected in a conical tube; cells were rinsed with PBS and trypsinized. Cells were re-suspended in 1 mL PBS with protease inhibitors, equating to a protein concentration of approximately 1 mg/mL. 100 μL of resuspended cells were transferred to PCR tubes and incubated for 3 minutes in thermal cyclers preheated to the following temperatures: 37, 37, 44.7, 48.4, 52.3, 55, 58, 60.2, 63.3, 66.3, 70° C. Cells were lysed by freeze-thaw and centrifuged at 21.1 k RCF for 20 minutes at 4° C. Supernatants were removed to a fresh 0.5 mL Eppendorf tube.

Supernatant from the duplicate 37° C. treatment condition was used to determine protein concentration through BCA assay. This allowed for the quantitative transfer of 50 μg of protein in each of the remaining tubes to a fresh 1.5 mL Eppendorf tube. Proteins were denatured with 7 M urea, reduced with DTT and alkylated with iodoacetamide. Urea was diluted to a concentration of <1M with Tris pH 8.1 and proteins were digested with proteomics grade trypsin. Peptides were acidified and desalted via solid-phase extraction and evaporated by vacuum centrifugation. Each temperature treatment was differentially labeled using TMT-10-plex reagent.

TMT LC-MS/MS Analyses

The Orbitrap Fusion was operated with an Orbitrap MS1 scan at 120K resolution and an AGC target value of 500K. The maximum injection time was 100 milliseconds, the m/z range was 350 to 1300 and the dynamic exclusion window was 30 seconds. Precursor ions were selected for MS2 using quadrupole isolation (0.6 m/z isolation width) in a "top speed" (3 second duty cycle), data-dependent manner. Ion charge states of +2 through +5 were selected for MS2 by collision induced dissociation (CID) fragmentation (32% CID energy) and ion trap analysis. The MS2 scan maximum injection time was 60 milliseconds and AGC target value was 8K. MS2 fragment ions were selected for synchronous precursor selection (SPS)-MS3 analysis in a top 10 data-dependent manner. MS3 scans were generated through higher energy collision-induced dissociation (HCD) fragmentation (55% HCD energy) and Orbitrap analysis at 60K resolution, with a scan range of 110 to 750 m/z. The MS3 scan maximum injection time was 200 milliseconds and AGC target value was 50K.

Click Chemistry Sample TCA Precipitation and LC-MS/MS Analyses 40 million cells were plated into a total of 3-15 cm dishes per treatment condition and allowed to adhere overnight. Cells were treated for 2 h with DMSO, 2 μM Y102, or 2 μM azide-tagged Y102. Following treatment, cells were washed with PBS, trypsinized, and resuspended in 850 μL Urea Lysis Buffer (8 M urea, 200 mM Tris pH 8, 4% CHAPS, 1 M NaCl) from the Click-iT Protein Enrichment Kit (Molecular Probes). Samples were incubated on ice for 10 minutes prior to sonication 6×3 seconds. Lysates were centrifuged at 10,000 g for 10 min, then 800 μL of the lysate was added to 200 μL of alkyne-bound resin slurry and 1 mL of catalyst solution containing copper (II) sulfate at a final concentration of 1 mM. Slurries were rotated end-over-end at room temperature for 18 hours. Following this, samples were reduced using 1M DTT and 7.4 mg/mL of iodoacetamide, stringently washed using SDS wash buffer, 8 M urea, and 20% acetonitrile, precipitated in 20% TCA, and washed in 10% TCA and cold acetone. Precipitated proteins were digested to peptides with trypsin and identified by LC-MS/MS on an Orbitrap Fusion as described below.

LC-MS/MS Analyses of TCA Precipitated Material

LC-MS/MS analysis was performed on an Orbitrap Fusion Tribrid mass spectrometer (Thermo Fisher Scientific, San Jose, CA) equipped with an EASY-nLC 1000 ultra-high-pressure liquid chromatograph (Thermo Fisher Scientific, Waltham, MA). Peptides were dissolved in loading buffer (5% methanol (Fisher)/1.5% formic acid) and injected directly onto an in-house pulled polymer coated fritless fused silica analytical resolving column (40 cm length, 100 μm inner diameter; PolyMicro) packed with ReproSil, C18 AQ 1.9 μm 120 Å pore (Dr. Maisch). Samples were separated with a 90-minute gradient of 4 to 33% LC-MS buffer B (LC-MS buffer A: 0.125% formic acid, 3% ACN; LC-MS buffer B: 0.125% formic acid, 95% ACN) at a flow rate of 330 nL/min. The Orbitrap Fusion was operated with an Orbitrap MS1 scan at 120K resolution and an AGC target value of 500K. The maximum injection time was 100 milliseconds, the scan range was 350 to 1500 m/z and the dynamic exclusion window was 15 seconds (+/−15 ppm from precursor ion m/z). Precursor ions were selected for MS2 using quadrupole isolation (0.7 m/z isolation width) in a "top speed" (2 second duty cycle), data-dependent manner. MS2 scans were generated through HCD fragmentation (29% HCD energy) and Orbitrap analysis at 15K resolution. Ion charge states of +2 through +4 were selected for HCD MS2. The MS2 scan maximum injection time was 60 milliseconds and AGC target value was 60K.

Peptide Spectral Matching and Bioinformatics

Raw data were searched using COMET against a target-decoy version of the human (*Homo sapiens*) proteome sequence database (UniProt; downloaded 2013; 20,241 total proteins) with a precursor mass tolerance of +/−1.00 Da and requiring fully tryptic peptides with up to 3 missed cleavages, carbamidomethyl cysteine as a fixed modification and oxidized methionine as a variable modification (48). For TMT experiments, the TMT reagent mass was searched as a static modification on lysine residues and peptide N-termini. The resulting peptide spectral matches were filtered to <1% false discovery rate (FDR) by defining thresholds of decoy hit frequencies at particular mass measurement accuracy (measured in parts-per-million from theoretical), XCorr and delta-XCorr (dCn) values. TPP-TR analyses were performed using the R statistical programming language (49).

siRNA Knockdown

To knockdown BORCS6, cells were plated at 200,000 cells/well in six-well plates or 50,000 cells/well on pre-coated PDL coverslips in 24-well plates and allowed to adhere overnight. The next day, cells were transfected with negative control siRNA (Ambicon; #AM4611) or siRNA targeting BORCS6 (Invitrogen; HSS123247) at a final concentration of 2 pmol/μL and lipofectamine 2000 (Invitrogen) in Opti-MEM medium (Gibco), and the mixture was incubated for 20 minutes at room temperature prior to drop-wise addition to cells. 24 hours after transfection reagents were added to culture, medium was removed and replaced with normal growth medium. Cells were incubated for a total of 72 hours before collection.

Stable Transfection of BORCS6 in U87-MG Cells

To establish U87-MG cells overexpressing BORCS6, cells were plated at 100,000 cells/well in a 12-well plate and allowed to adhere overnight. The next day, cells were transfected with pcDNA3.1 empty vector or pBORCS6 (GenScript) at a final concentration of 8 ng/μL and lipofectamine 2000 (Invitrogen) in Opti-MEM medium (Gibco), and the mixture was incubated for 20 minutes at room temperature prior to drop-wise addition to cells. 24 hours after transfection reagents were added to culture, medium was removed and replaced with normal growth medium containing 1000 μM G418. After several days, pBORCS6 underwent clonal selection; expression was confirmed by immunofluorescence.

Identification of Tool Compound Y102 as Synthetic Lethal In Vitro with Loss of NF1 Protein A high-throughput screen in *Saccharomyces cerevisiae* lacking a yeast homologue of NF1, IRA2 (ira2Δ) was developed and carried out to identify tool compounds that elicited synthetic lethality with NF1 loss (15). ira2Δ yeast have increased RAS-GTP, which results in increased MAPK and PKA signaling analogous to the pathways that are activated in NF1-deficient Schwann cells (17). The yeast strains used in these screens also lacked the ERG6 gene to facilitate drug retention (18).

Figure 1B:
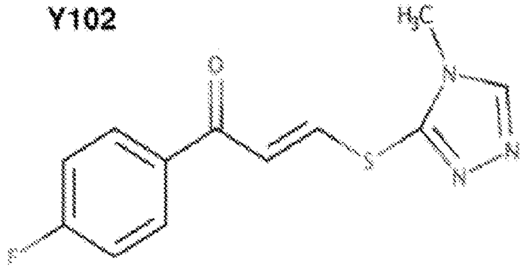
Figure 1C:
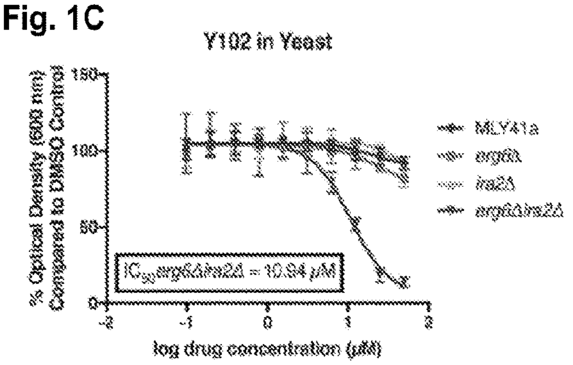
Figure 1D:
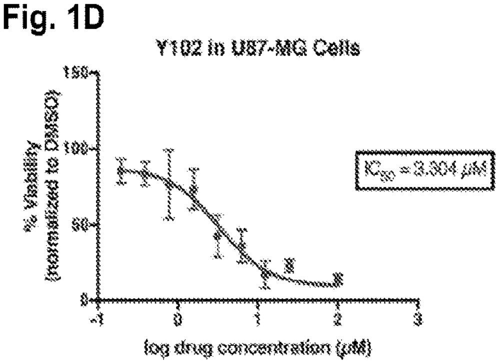
Figure 1E:
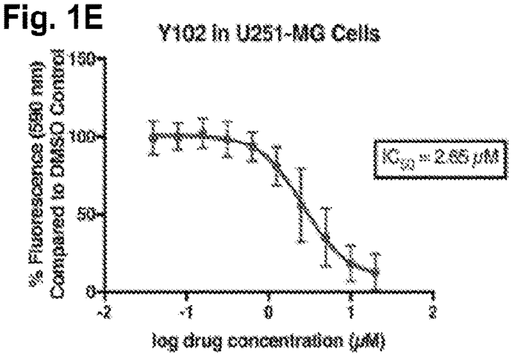
Figure 1F:
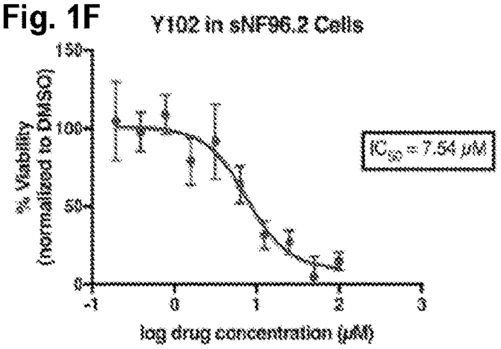
Figure 1G:
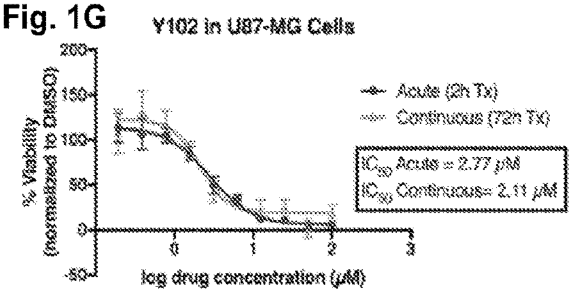
Figure 1H:
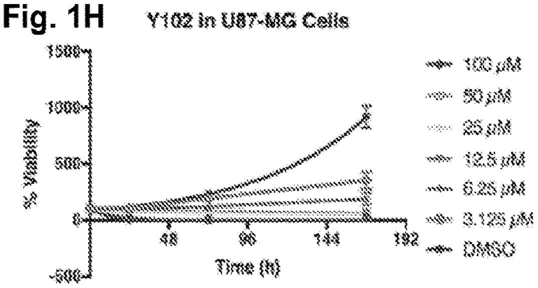

More than 5,100 structurally diverse compounds selected from and representative of a >340,000-compound library were screened. It was hypothesized that a synthetic lethal screen with yeast cells that lack an NF1 homolog will identify tool compounds that will be selective for NF1-deficient human tumor cells. In this screen, a compound was considered a hit if ira2Δ yeast exhibited slow growth or death at concentrations that had no effect on the growth of control yeast (FIG. 1A). Utilizing this approach, tool compound Y102 was found to have an inhibitory effect on the erg6Δira2Δ yeast at concentrations that had no effect on the control strains (FIG. 1B-C). To determine whether Y102 was also effective in human tumor cells, the efficacy of Y102 was evaluated in two NF1-deficient human cancer cell line models of glioblastoma, U87-MG and U251-MG, and an NF1-deficient Neurofibromatosis type 1-associated MPNST cell line sNF96.2. U87s are considered a human glioblastoma cell line of unknown origin (19). U87-MG cells are NF1-deficient due to elevated proteasomal degradation of the NF1 protein and serve as a model of NF1-deficiency in the context of this work (9). It was found that all three NF1-deficient cell lines were sensitive to Y102 treatment (FIG. 1D-F). It was also found in U87-MG cells that acute treatment of 2 hours resulted in the same degree of growth inhibition compared to continuous treatment for 72 hours (FIG. 1G). To understand the long-term efficacy of Y102 treatment in vitro, the effect of Y102 treatment on cell proliferation after seven days of treatment was investigated. Cell proliferation was inhibited by continuous Y102 treatment with increasing concentrations starting at 3.125 μM Y102 (FIG. 1H).

Y102 Treatment Results in Increased Expression of Autophagy and Oxidative Stress Markers To identify the mechanism of action of Y102-mediated cell death, expression of proteins associated with pathways that, when altered, can lead to cell death following Y102 treatment: DNA damage, apoptosis, proteasome inhibition, and autophagy (also referred to as macroautophagy) was examined (20-22). Expression of the DNA damage marker γ-H2AX, a histone H2A variant that is phosphorylated following the generation of double- and single-stranded DNA breaks was examined (20). There was no significant change in γ-H2AX expression following Y102 treatment (FIG. 8A). This suggested that Y102 was not mediating cell death through a DNA damage response pathway in which an increase in the formation of DNA breaks would be observed. We examined apoptotic cell death following Y102 treatment by monitoring the cleavage of caspase-3 (21). No difference in the amount of cleaved caspase-3 between Y102 treatment and the vehicle control was observed (FIG. 8B). This was confirmed by western immunoblotting for PARP, an enzyme that is cleaved by caspase-3 under apoptotic conditions (FIG. 8C) (23). This result suggested that the mechanism of Y102-mediated cell death is not by caspase-3-mediated apoptosis.

The labeling of proteins with ubiquitin to mark them for degradation can trigger cell death that is mediated by the proteasome, the unfolded protein response, or autophagy. To determine whether Y102 acted as a direct inhibitor of the proteasomal active sites, the activity-based, broad-range fluorescent inhibitor MV-151, which can bind to and inhibit all three subunits of the proteasome were utilized (24). A competitive binding assay in which cells were treated with DMSO, Y102, or a combination of proteasome inhibitors to serve as a positive control was performed (FIG. 8D). Inhibition of the proteasomal subunits was only observed following treatment with our positive controls and not with Y102, as indicated by the presence of MV-151 in the Y102 treated sample, eliminating proteasome inhibition as a mechanism of action of Y102-mediated cell death.

Figure 2A:
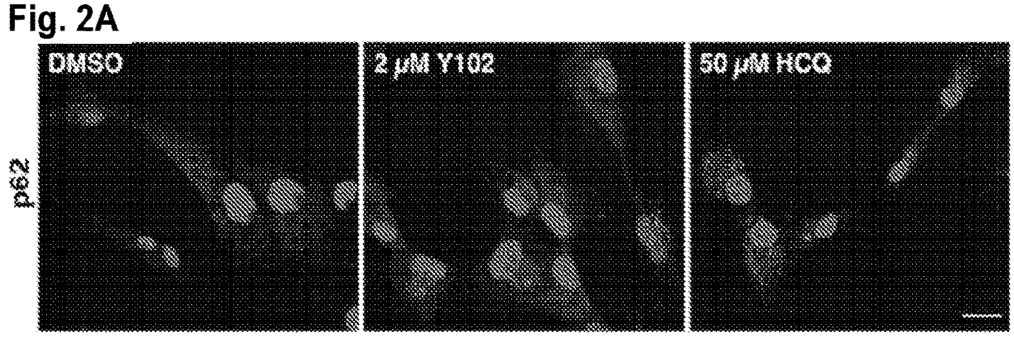
FIGS. 2A-2G: Y102 treatment results in increased expression of autophagy and oxidative stress markers and alters the mitochondrial network.
Figure 2B:
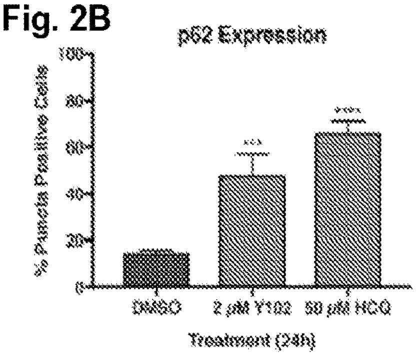
Figure 2C:
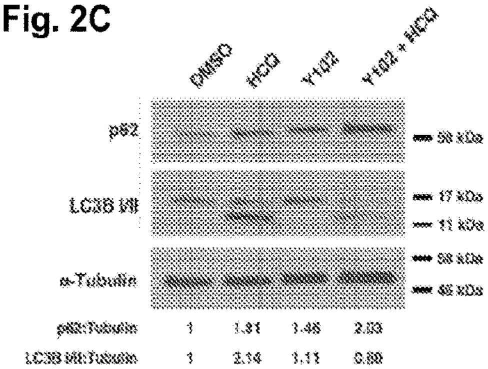

The impact of Y102 treatment on autophagic processes was examined by surveying expression of the adaptor protein sequestosome-1 (p62), a shared marker of autophagy and oxidative stress perturbations (22, 25). p62 recognizes and binds to ubiquitin on cargo marked for degradation either by autophagy or the proteasome; further, phosphorylation of NFκB following oxidative stress induction results in the upregulation of p62 protein (25, 26). Y102 treatment increased expression of p62 compared to DMSO (FIG. 2A-B). It was also found that p62 expression with Y102 treatment was similar to that observed using the late-stage autophagy inhibitor hydroxychloroquine (HCQ) (27). The effect of Y102 on the lipidation state of microtubule-associated protein light chain 3 (LC3), another autophagy marker, was also examined (28). Cytosolic LC3-I is converted to LC3-II via phosphatidylethanolamine addition, and LC3-II is recruited to autophagosome membranes (29). When autophagy is inhibited at a stage following the lipidation of LC3-I with compounds like HCQ, accumulation of LC3-II is detected via western immunoblotting; however, when autophagy is stimulated and unhindered, LC3-II is degraded within the autolysosome and only LC3-I is detectable (30). Based on this knowledge, it was hypothesized that LC3-II would accumulate after Y102 treatment if Y102 treatment resulted in inhibition of macroautophagy. To test this, U87-MG cells were treated with Y102 for 12 hours, followed by HCQ co-treatment for an additional 12 hours, for a total of 24-hour treatment (FIG. 2C). It was found that, while p62 expression increased with Y102 or HCQ treatment, Y102 treatment alone did not result in LC3-II accumulation. All treatments with HCQ present resulted in LC3-II accumulation, suggesting that, while HCQ and Y102 treatment both increase expression of p62, the mechanisms of action of Y102 and HCQ differ and Y102 may not be a macroautophagy inhibitor.

Figure 2D:
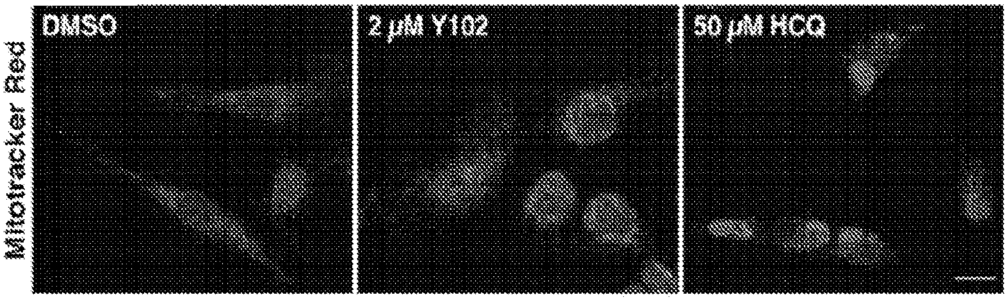
Figure 2E:
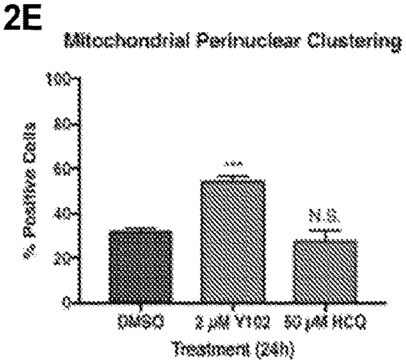

Previous studies have shown that RAS dysregulated tumors, which include NF1-deficient tumors, depend on autophagy to modulate accumulation of oxidative stress-induced damaged mitochondria, and defective autophagic clearance results in the accumulation of abnormal mitochondria (31). To investigate whether Y102 treatment resulted in an abnormal mitochondrial phenotype, the membrane potential based fluorescent probe MitoTracker Red CMXRos was used (FIG. 2D-E). While DMSO treated cells had a highly structured network of mitochondria, Y102 treated cells exhibited perinuclear clustering of the mitochondria, something not observed with HCQ treatment.

Figure 2F:
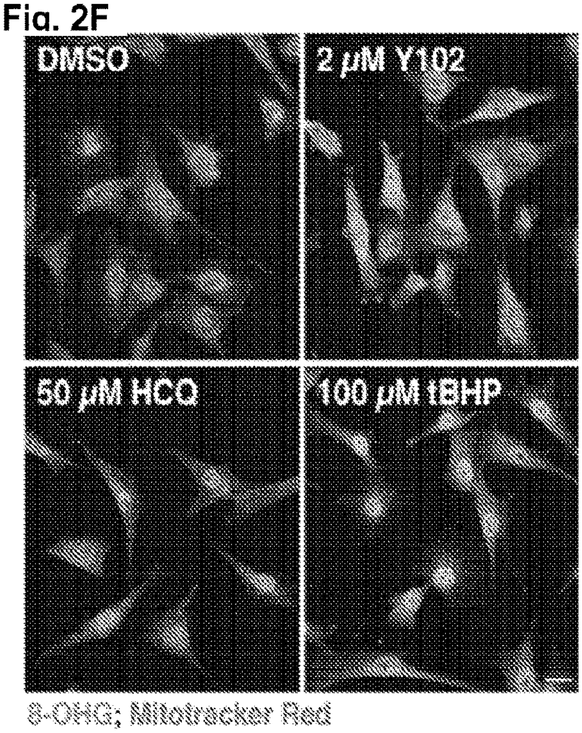
Figure 2G:
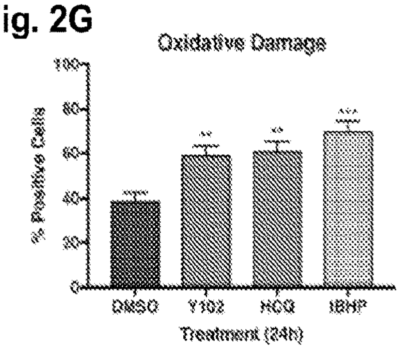

To investigate whether Y102 treatment resulted in an increase in oxidative damage within NF1-deficient cells, 8-hydroxyguanosine (8-OHG), an oxidative stress-induced DNA damage marker for both nuclear and mitochondrial DNA, was probed for (25, 32). Y102 treatment resulted in an increase in 8-OHG compared to DMSO, suggesting that there was an increase in oxidative stress and subsequent damage following Y102 treatment (FIG. 2F-G). Localization of 8-OHG indicated that the oxidative stress-induced damage affected both nuclear and mitochondrial DNA, as 8-OHG expression co-localized in both the mitochondria in the cytoplasm and the nucleus. Together, these findings suggest a potential mechanism of action of Y102 resulting in a defect to clear mitochondria by an autophagic process.

Y102 Treatment Alters Localization of the Mitophagy Receptor BNIP3L/Nix

Figure 3A:
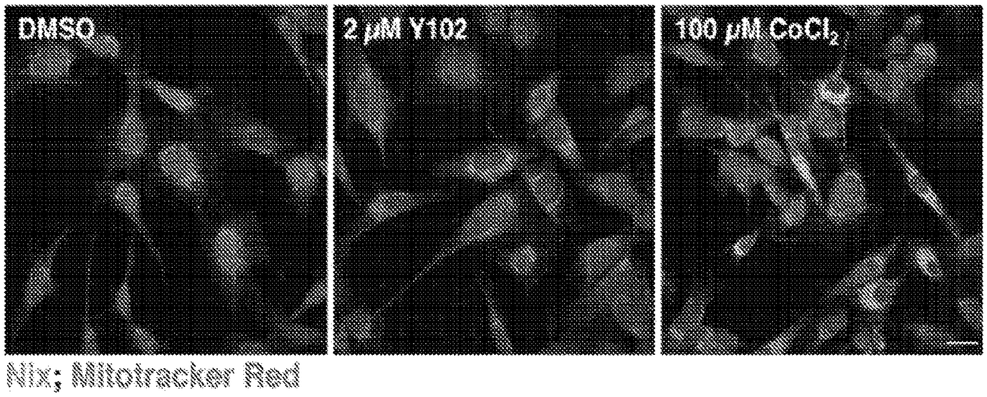
FIGS. 3A-3E: Treatment with Y102 prevents lysosome-mediated mitochondrial clearance.
Figure 3B:
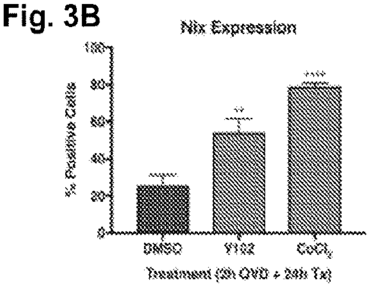
Figure 3C:
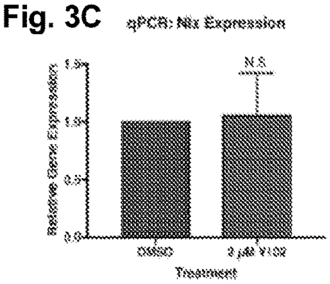
Figure 3D:
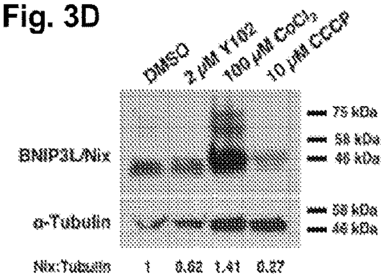

Though autophagy was initially thought to be a non-selective process, studies have demonstrated that there are also selective forms of autophagy (33). While p62 can play a role in some forms of mitochondrial degradation via autophagy (known as mitophagy), it can also play a role in a host of other selective autophagy processes, as well as non-selective autophagy (33). It was determined whether Y102 treatment resulted in an effect on mitophagy by examining expression of a mitophagy-specific receptor BNIP3L/Nix (34). BNIP3-mediated mitophagy is reported to occur following perinuclear clustering and fragmentation of the mitochondria (35). With Y102 treatment, an increase in expression of BNIP3L/Nix on the mitochondria compared to DMSO control was observed (FIG. 3A-B). This localization of BNIP3L/Nix with Y102 treatment was similar to what was observed after treatment with the mitophagy inducer CoCl2. To address whether Y102 treatment resulted in increased expression of BNIP3L/Nix or only a change in its localization following Y102 treatment, protein expression levels using Western immunoblotting were analyzed (FIG. 3C). There was little difference in BNIP3L/Nix protein levels between Y102 treated and DMSO treated cells, suggesting that there was not an increase in BNIP3L/Nix protein expression with Y102 treatment but rather a change in its localization. To confirm this, qPCR was performed to examine transcript levels of BNIP3L/Nix (FIG. 3D). Again, there was little difference in BNIP3L/Nix RNA levels between DMSO and Y102 treatment, suggesting that Y102 treatment resulted in a change in the localization of BNIP3L/Nix to the mitochondria.

Y102 Treatment Prevents Lysosomal-Directed Mitochondrial Clearance

Figure 3E:
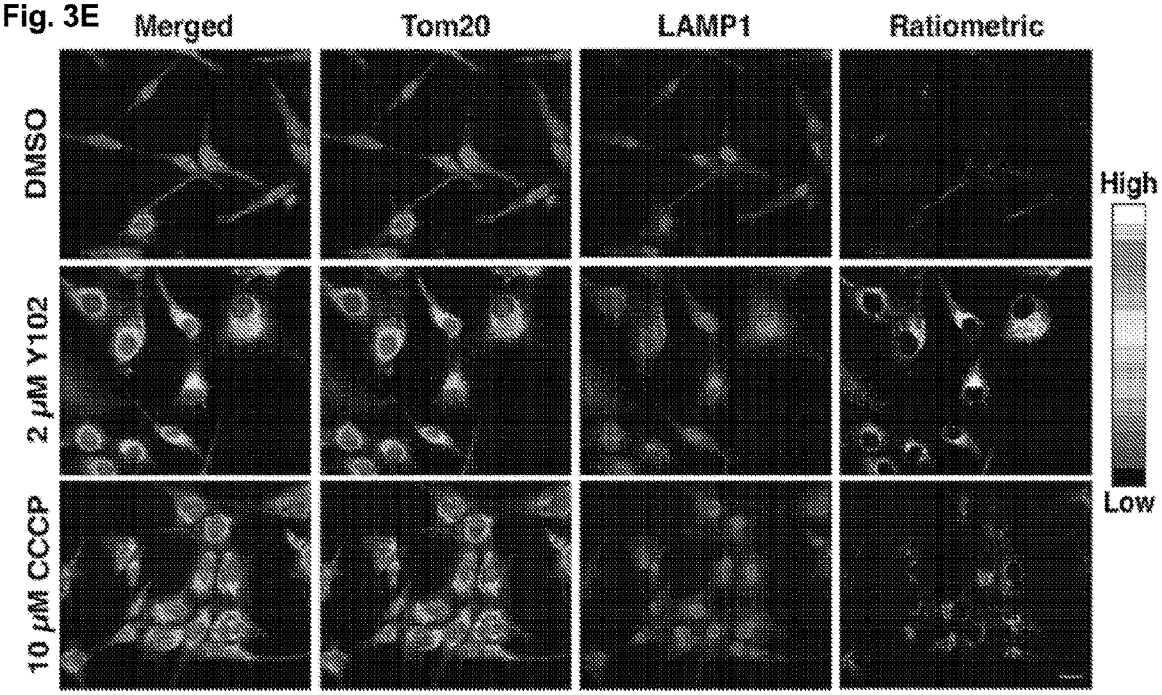

Late stages of mitochondrial clearance when the mitochondria-selective autophagosomes fuse with acidic lysosomes to form the autolysosome were investigated due to further mechanistic analysis into Y102-mediated cell death. Late stage mitochondrial clearance was investigated by examining expression and localization of lysosomes with mitochondria. An increase in lysosome expression was observed following Y102 treatment, and these lysosomes were found to localize in the perinuclear region of the cell (FIG. 3E). Colocalization between lysosomes and mitochondria was observed with Y102 treatment, as determined by ratiometric analysis of the obtained images and by the observance of yellow fluorescence, indicative of a co-localization between red and green fluorescence, using confocal microscopy (FIG. 3E). These data suggest that Y102 treated cells are unable to effectively traffic lysosomes out of the cell, indicated by the perinuclear clustering of the lysosomes, and the clustering of the mitochondria suggests that the mechanism of Y102-mediated cell death may be linked to a defect in lysosomal-directed mitochondrial clearance.

Implementing a Multi Pronged Approach to Identify the Cellular Target(s) of Y102

Figure 4A:
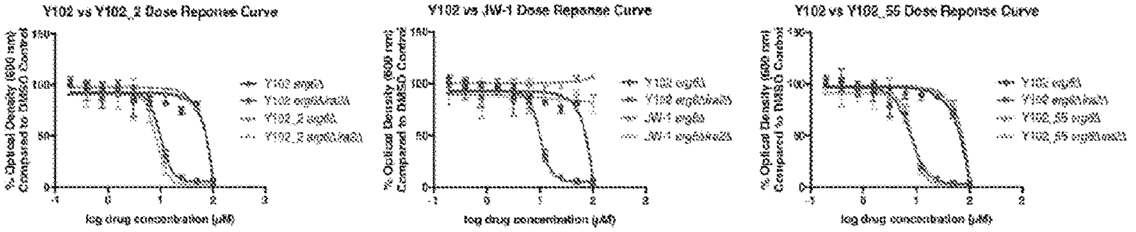
FIGS. 4A-4H: Identification of potential targets of Y102 using a multipronged proteomics approach.
Figure 4B:
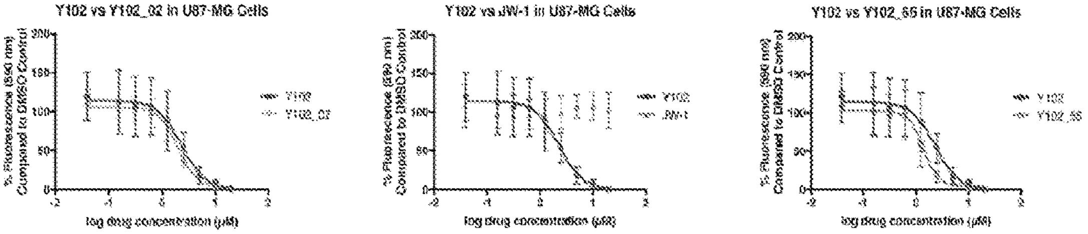
Figure 4C:
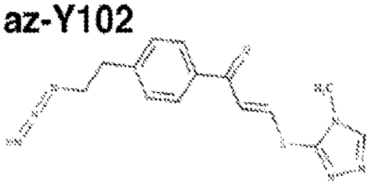
Figure 4D:
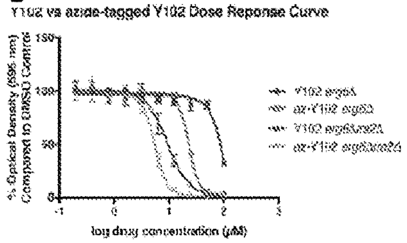
Figure 4E:
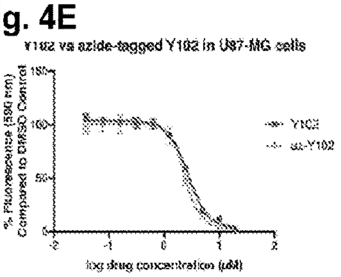

It was observed that the effects of Y102 were irreversible after a 2 hour treatment and hypothesized that this irreversibility could be leveraged to identify targets of Y102 using a click chemistry-enriched proteomics approach (36). Structure-activity relationship studies for Y102 was carried out in order to identify the key structural components of the compound required for its activity, with the ultimate goal of identifying a site on Y102 that could be modified with an azide group. A total of twenty analogs of Y102 was designed, most of which had relatively little effect on the efficacy of the analog in both yeast and mammalian platforms, though some modifications resulted in complete loss of activity (Table 1, FIGS. 4A-B; FIGS. 9A-9D). Based on findings from these structure-activity relationship studies, an azide-tagged version of Y102 was designed to use in a click-chemistry enhanced pulldown of proteins that bound Y102 (az-Y102; FIG. 4C). IRA2-deficient yeasts were found to be preferentially sensitive to az-Y102 as was observed with the parent compound Y102, and a similar efficacy between Y102 and az-Y102 was observed in the U87-MG human tumor cell line model, making it a comparable analog to use in the target identification strategy (FIG. 4D-E).

Figure 4F:
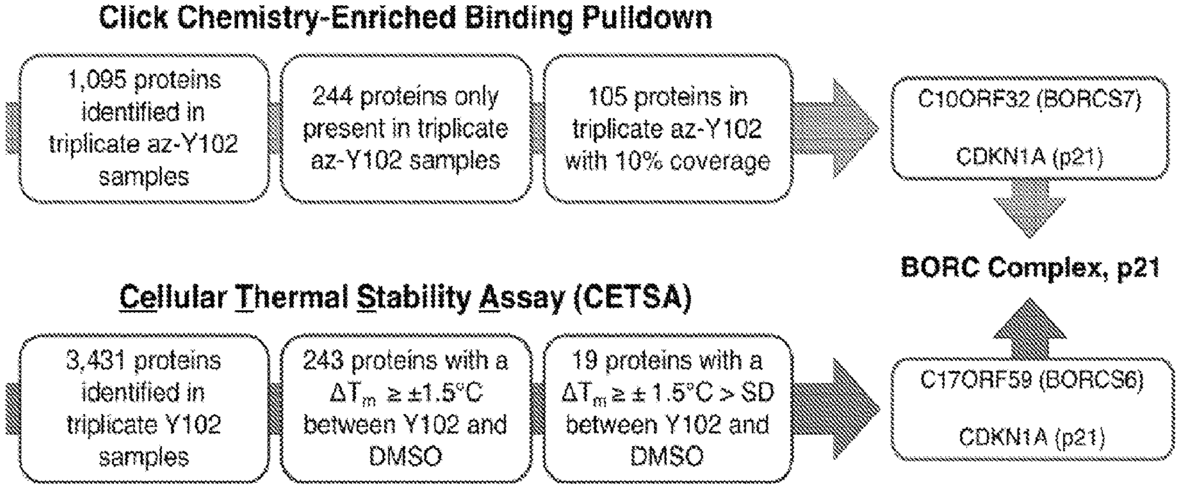
Figure 4G:
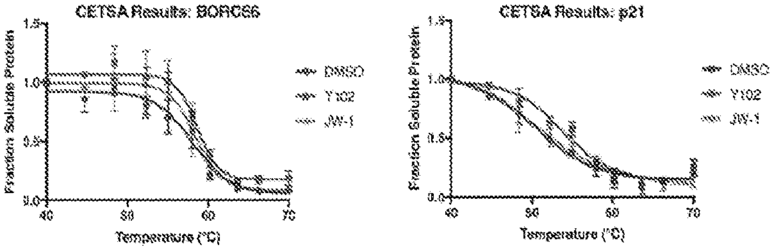
Figure 4H:
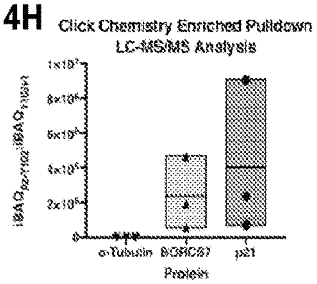

U87-MG cells were treated with vehicle DMSO, parent compound Y102, and az-Y102 for two hours, and the lysates were incubated with a resin-bound alkyne in the presence of copper sulfate to covalently pulldown all proteins bound to az-Y102. These proteins were digested using trypsin, and the peptides were eluted. Utilizing liquid chromatography-tandem mass spectrometry (LC-MS/MS), the peptide intensities and observable peptides of a protein were measured, and the ratios were compared between az-Y102 and the controls Y102 (no azide tag) and DMSO. Using this procedure, 105 proteins present in all az-Y102 samples were identified in triplicate experiments, but not identified in the controls, with >10% percent of the protein identified in the peptide fragments analyzed. Simultaneously, a second, but separate, proteomics approach known as a cellular thermal shift assay (CETSA) was used to identify potential targets of Y102 by comparing the thermal stability proteome profiles between Y102 treated cells and control treated cells (37). Comparison between DMSO and Y102 proteome-wide thermal stability profiles identified 19 proteins with a statistically significant difference (p-value≤0.100) of their melting points between Y102 and DMSO (ΔTm; FIG. 4F). Upon comparison between the two proteomics approaches, two potential targets were identified: the BORC complex, determined by the identification of two subunits BORCS6 and BORCS7, and the cell cycle regulator CDKN1A/p21 (FIGS. 4G-H).

The BORC Complex is a Potential Vulnerability in NF1-Deficient Cells

BORCS6 is part of the multiprotein BLOC-one-related complex (BORC) comprised of eight proteins (40). The BORC complex is associated with the cytosolic side of lysosomes and is required for the transport of lysosomes from the perinuclear region to the cell periphery along microtubules through anterograde transport. Recent work has demonstrated that lysosomes play important roles outside of their function as degradative organelles, including functions in plasma membrane repair, cell adhesion and migration, tumor invasion and metastasis, gene regulation, and metabolic signaling (41). A loss of various BORC complex subunits is reported to result in perinuclear clustering of LAMP-1 positive lysosomes (40). Trafficking of lysosomes to the cell periphery promotes cell transcription, translation, and metabolic processes associated with proliferation (42).

Figure 5A:
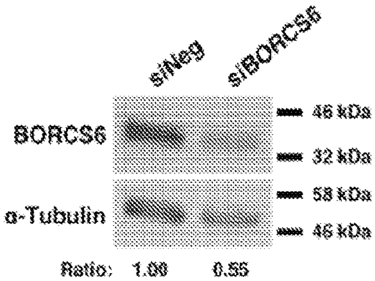
FIGS. 5A-5B: Knockdown of a BORC complex subunit recapitulates the phenotypes of Y102 treatment.
Figure 5B:
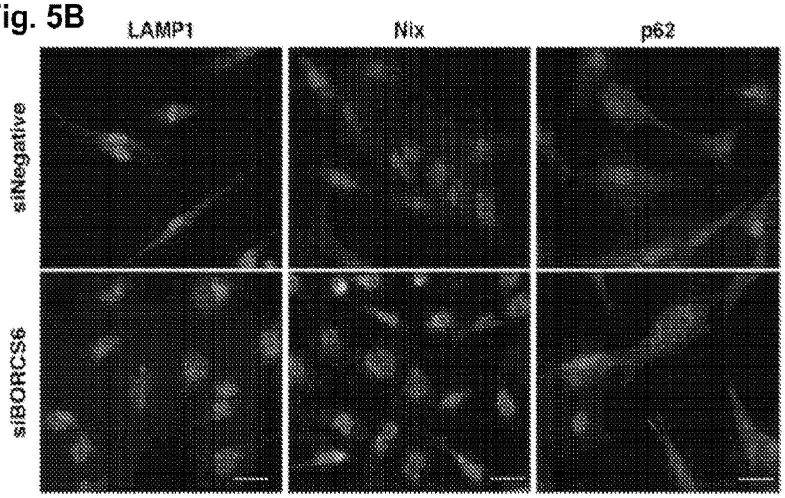

It was hypothesized that prevention of lysosome trafficking to the cell periphery through inhibition of the BORC complex in NF1-deficient cells could recapitulate the phenotypes observed after Y102 treatment. To test this hypothesis, we knocked down one subunit of the BORC complex by using siRNA against BORCS6 (FIG. 5A). As previously reported, knockdown of BORCS6 resulted in perinuclear clustering of the lysosomes and an increase in p62 puncta, and also recapitulated the phenotypes observed with Y102 treatment (FIG. 5B and see below) (43). Knockdown of BORCS6 also resulted in a similar increase in alteration in Nix expression as observed with Y102 treatment (FIG. 5B).

Figure 6A:
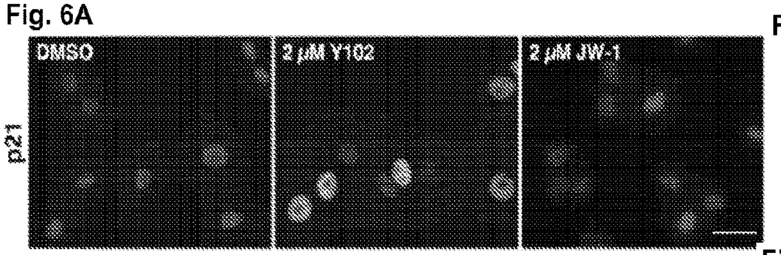
FIGS. 6A-6J: Knockdown of a BORC complex subunit or treatment with Y102 leads to increased p21 expression and nuclear size (FIG. 6A) U87-MG cells were treated for 24 h with DMSO, 2 μM Y102, or 2 μM JW-1. Cells were stained for p21, a regulator of the cell cycle (green). DAPI was used to counterstain cell nuclei (blue). Scale bar=150 μm (FIG. 6B) Quantification of p21 positive cells. 100 cells were analyzed in triplicate experiments. Statistical analysis was performed as in FIG. 2B.
Figure 6E:
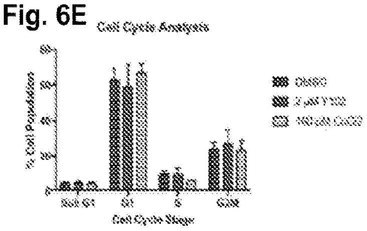
Figure 6B:
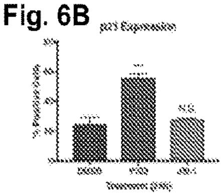
Figure 6C:
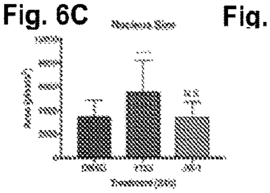
Figure 6D:
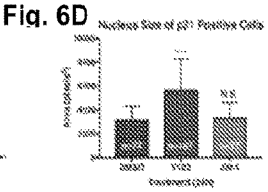
Figure 6F:
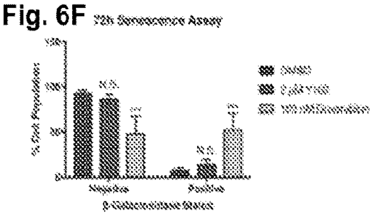
Figure 6G:
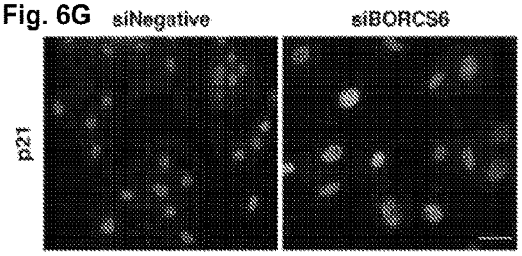
Figure 6H:
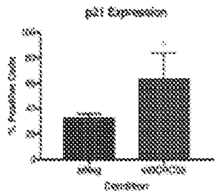
Figure 6I:
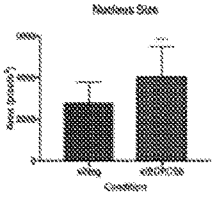
Figure 6J:
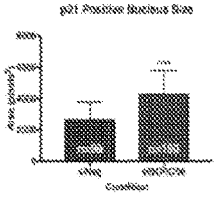

Knockdown of a BORC Complex Subunit or Treatment with Y102 Leads to Increased p21 Expression and Nuclear Size Because p21 was identified in the proteomics approaches, expression of p21 following Y102 treatment was examined. p21, also known as CDKN1A, is a regulator of the cell cycle through inhibition of cyclin-dependent kinases (CDKs) (38). p21 binding and inhibition of CDK4,6/cyclin-D, CDK2,1/cyclin-E, CDK2,1/cyclin-A, and CDK1/cyclin-Bcan leads to cell cycle arrest. Further, p21 expression can mediate cellular senescence by a ROS-based mechanism, which can lead to flattening of the cell, which is reflected in an increase in nuclear size and a decrease in DNA-associated fluorescence from [4,6-diamidino-2-phenylindole (DAPI)] (39). To determine whether p21 expression or nucleus size was altered with Y102 treatment, both p21 expression and nucleus size were analyzed via immunofluorescence (FIG. 6A-D). It was found that Y102 treatment resulted in an increase in p21 expression, an increase in nucleus size, and a correlation between increased nucleus size and p21 expression. As p21 plays a role in cell cycle regulation and cellular senescence, the cell cycle distribution indicated by DNA content and senescence using a senescence-associated β-galactosidase assay of cells following Y102 treatment was examined (FIG. 6E-F). In both instances, no indication of cell cycle arrest or senescence was found, indicating that while Y102 treatment resulted in an increase in p21 expression, that elevated levels of p21 did not result in cell cycle arrest or senescence. An increase in p21 expression and nucleus size following BORCS6 knockdown was also observed (FIG. 5A, FIG. 6G-J), suggesting that alterations in p21 expression may be a consequence of inhibition of the BORC complex.

The BORC Complex Interacts with Y102

Figure 7A:
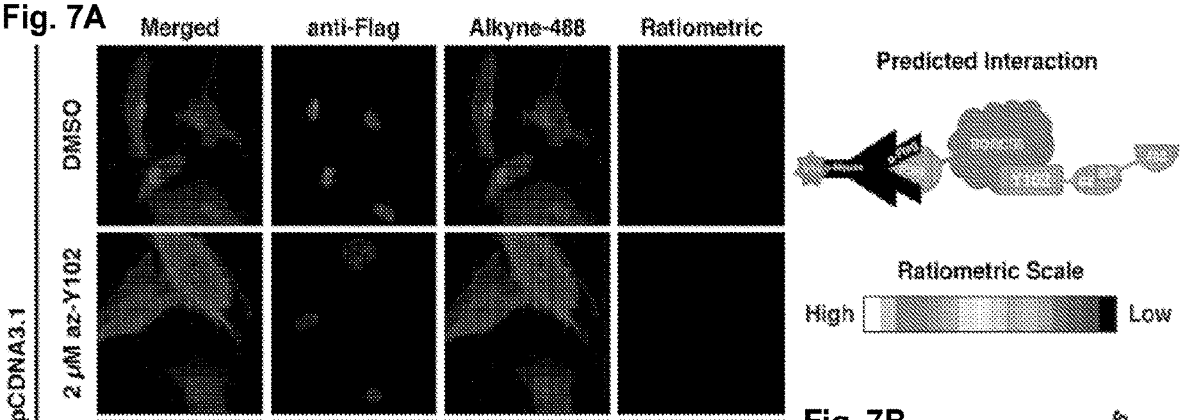
FIGS. 7A-7C: The BORC complex interacts with Y102.
Figure 7A:
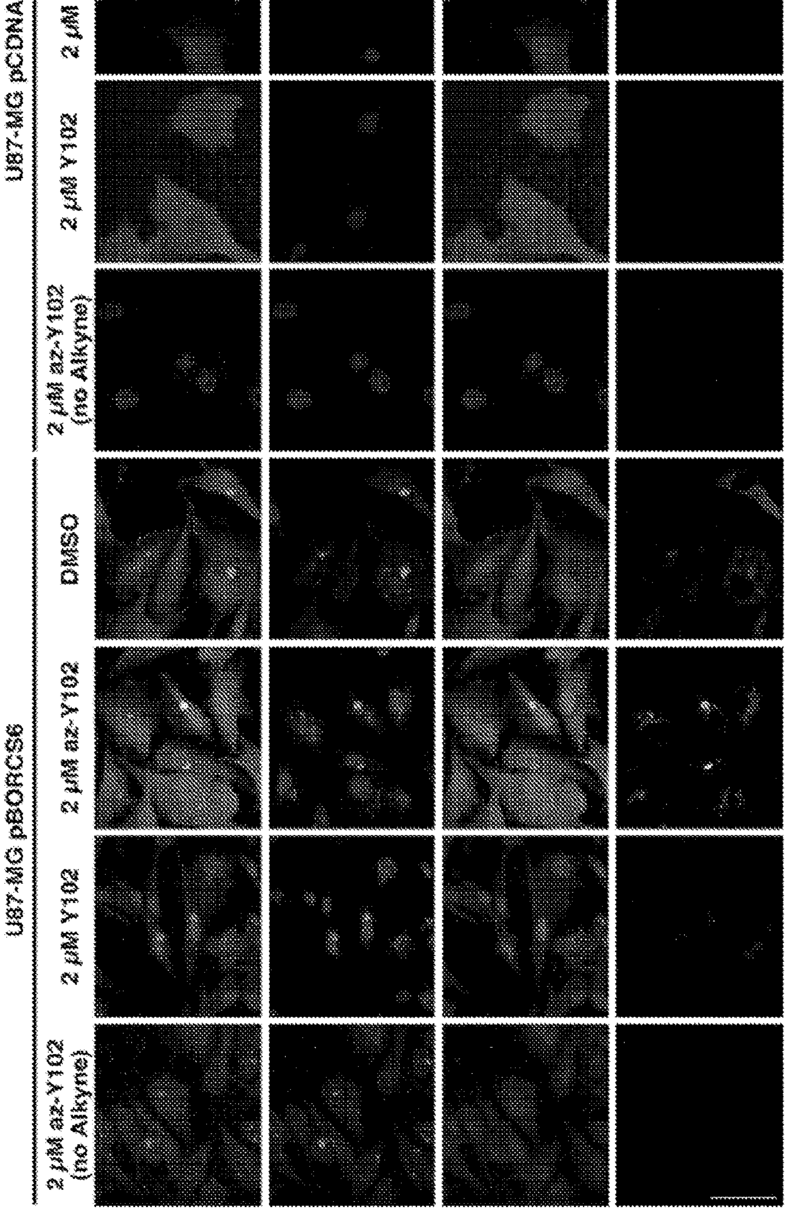
Figure 7B:
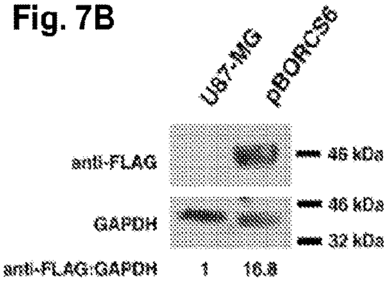
Figure 7C:
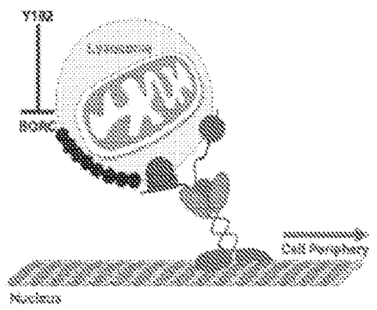
Figure 9A:
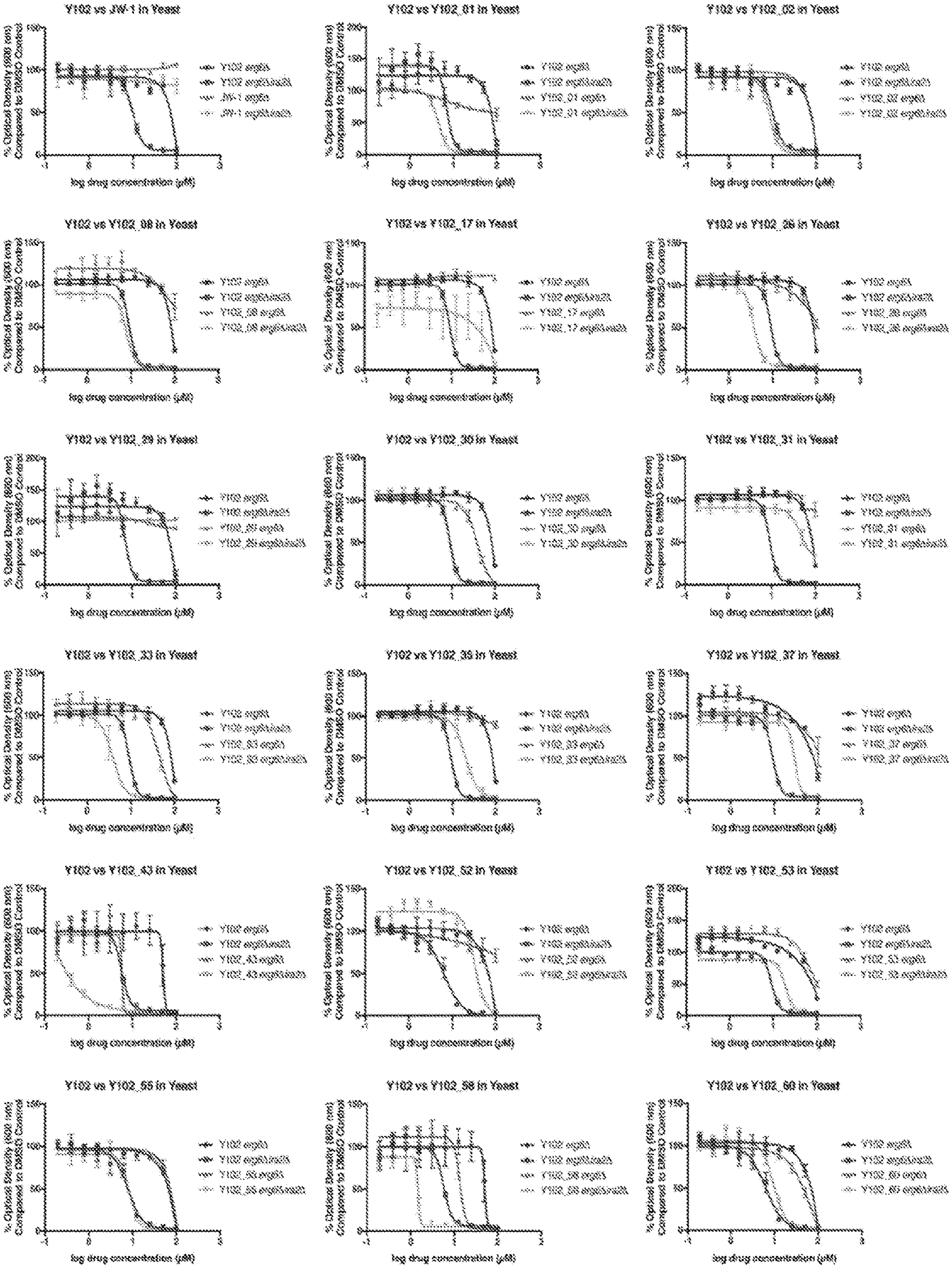
FIGS. 9A-9D: Structure-activity relationship studies comparing the parent compound Y102 to Y102 analogs.
Figure 9B:
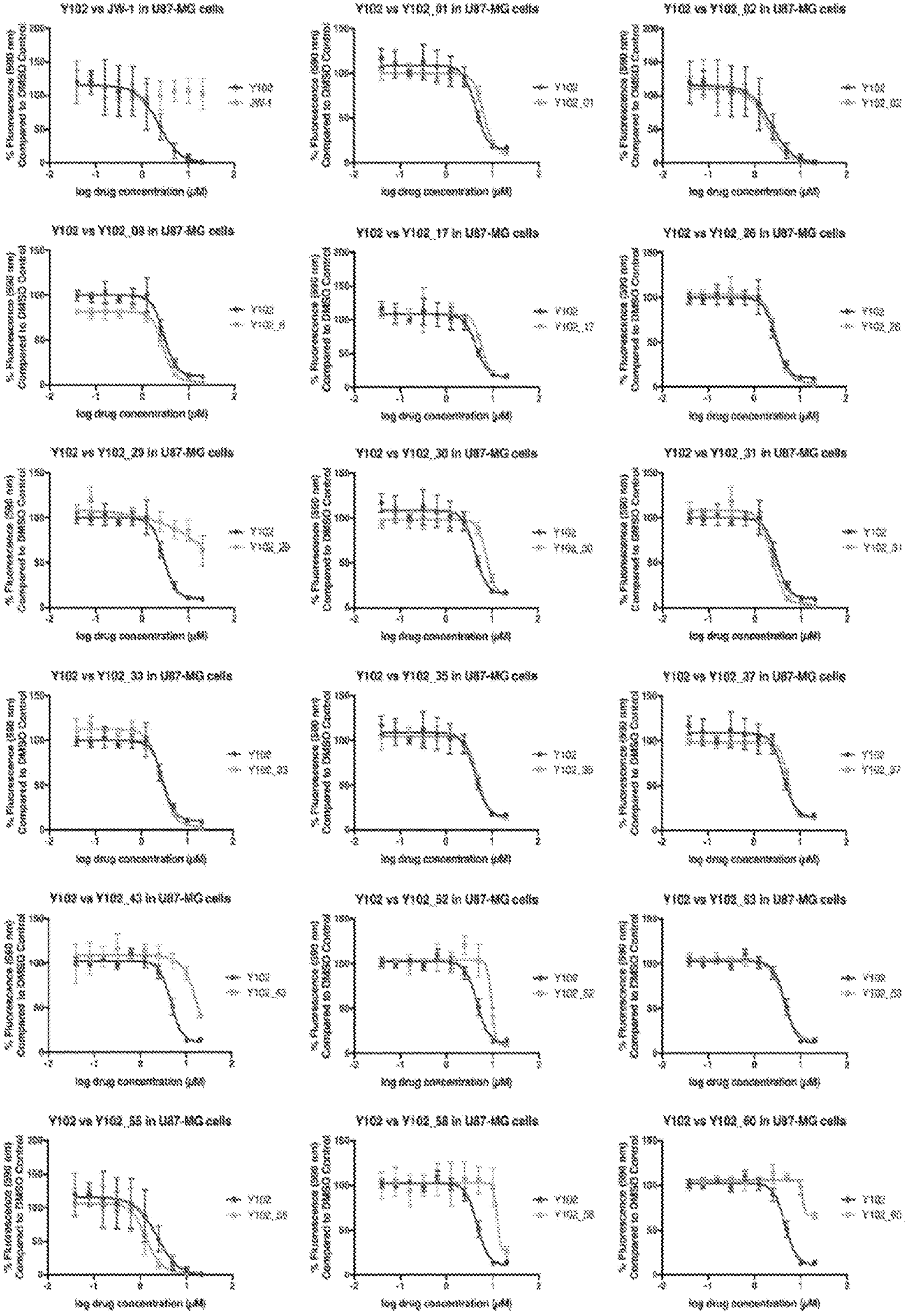
Figure 9C:
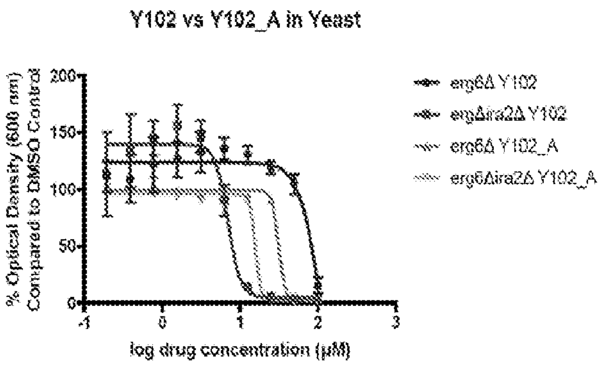
Figure 9C:
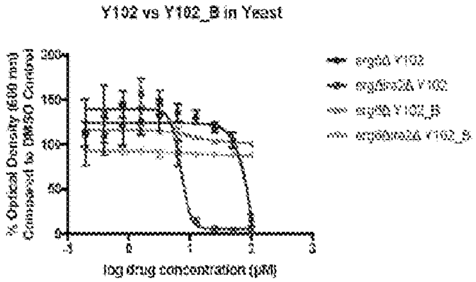
Figure 9D:
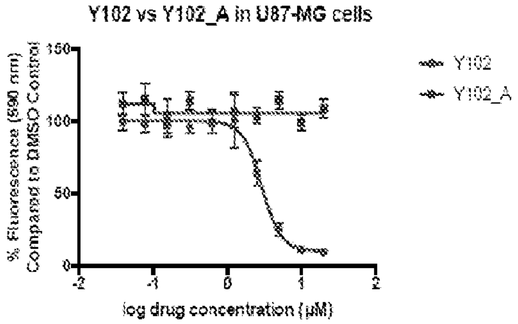
Figure 9D:
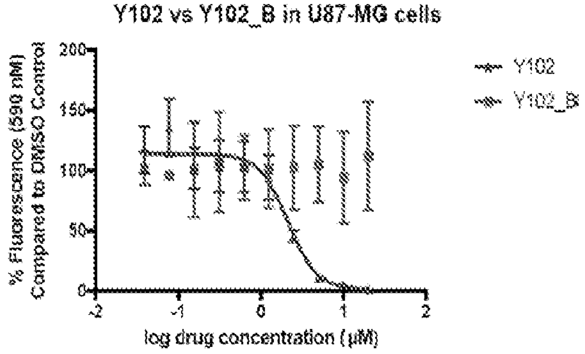

To confirm the interaction between Y102 and BORCS6, Flag-tagged BORCS6 or empty vector (EV) in U87-MG cells was overexpressed and cells were treated with az-Y102, Y102, or DMSO for two hours, following removal of the drug and incubation in media without vehicle or drugs for an additional 22 hours. (FIG. 7A). az-Y102 was labeled with alkyne-488 using click chemistry, while overexpressed BORCS6 was detected with anti-Flag. Confocal microscopy revealed that az-Y102 and BORCS6 colocalized in the cell, demonstrating that the cellular BORCS6 complexes are bound by Y102. Overexpression was confirmed via Western immunoblotting (FIG. 7B). These findings suggest a potential mechanism of action of Y102 via inhibition of the BORC complex (FIG. 7C).

Mechanism for Y102-Mediated Cell Death

The disclosure presented here demonstrates that Y102 alters lysosome positioning and impacts mitochondrial clearance in NF1-deficient cancer cells and is synthetic lethal with NF1 loss in an isogenic yeast model. It was determined that the effect of Y102 on the viability of cells is irreversible after 2 hours of treatment, and treatment with tool compound Y102 is effective in reducing the viability of an in vitro NF1-deficient human tumor cell line model. Further, proteomics approaches and immunofluorescent imaging support the BORC complex as a target of Y102. The working model is that Y102 prevents lysosome-directed mitochondrial clearance by preventing the normal function of the BORC complex. This results in the perinuclear clustering of the lysosomes, as we have observed with both Y102 treatment and knockdown of one subunit of the BORC complex.

RAS dysregulated cancer cells rely on a high turnover of mitochondria due to their susceptibility to oxidative stress-induced damage; as NF1-deficient cancer cells have dysregulated RAS, this can also be true of cancer cells with NF1 loss. An inhibition of mitochondrial clearance with Y102 treatment was observed, which leads to an accumulation of mitophagy-specific receptors and damaged mitochondria attributed to oxidative stress. Together, these findings suggest that inhibition of mitochondrial clearance via autophagy or prevention of lysosome distribution may be therapeutic strategies worth investigating further in the context of NF1-deficient tumors.

Alterations of p21 Expression with Y102 Treatment and BORC Knockdown

Two potential targets of Y102 using our dual proteomics approach were identified: p21 and the BORC complex. An increase in p21 expression was observed with both Y102 treatment and direct knockdown of a BORC subunit; however, there was no effect on cell cycle progression which is mediated by p21 expression. Further, there was no indication of Y102-induced senescence despite this observed increase. This raises the question as to why we detected p21 expression increased in both Y102-treated cells and siBORCS6-transfected cells. Increase in p21 expression both at the RNA and protein levels following treatment with autophagic-lysosomal inhibitors has been reported, suggesting that lysosome trafficking inhibition results in upregulation of p21 expression (44). Therefore, the increase observed with p21 following Y102 treatment and BORCS6 knockdown may be due to an effect on p21 expression following inhibition of autophagic lysosome inhibition. The changes in p21 levels could explain the identification of p21 in both of our proteomic approaches.

BORC as a Potential Vulnerability in NF1-Deficient Tumors

In addition to identifying a mechanism of action of Y102, this disclosure suggests the BORC complex as a potential therapeutic target in the context of cancer. Studies investigating the function of the BORC complex have found BORC to be responsible for lysosomal positioning in the cell, and knockdown of various subunits of the BORC complex have led to alterations in autophagy, and cell migration (40, 43). mTOR signaling plays a significant role in the regulation of the BORC complex and lysosomal trafficking has been shown to be linked to mTORC signaling in response to amino acids, and NF1-deficient cells are sensitive to mTORC1/2 inhibition (42, 45). The present disclosure demonstrates that knockdown of the BORCS6 subunit recapitulates the phenotype observed with Y102 treatment, including accumulation of macroautophagy and mitophagy-specific receptors, an increase in p21 expression and nucleus size, and the perinuclear clustering of lysosomes. Together, the data presented in this disclosure suggest that BORCS6 is a target of Y102, and inhibition of the BORC complex is a potential vulnerability of NF1-deficient tumors.

REFERENCES

1. Ratner N, Miller S J. A RASopathy gene commonly mutated in cancer: the neurofibromatosis type 1 tumour suppressor. Nat Rev Cancer. 2015; 15:290-301.
2. Walker J A, Upadhyaya M. Emerging therapeutic targets for neurofibromatosis type 1. Expert Opinion on Therapeutic Targets. 2018; 22:419-37.

3. Allaway R J, Gosline S J C, La Rosa S, Knight P, Bakker A, Guinney J, et al. Cutaneous neurofibromas in the genomics era: current understanding and open questions. British Journal of Cancer. Nature Publishing Group; 2018; 118:1539-48.
4. Korf B R. Malignancy in Neurofibromatosis Type 1. The Oncologist. 2000; 5:477-85.
5. Avery R A, Katowitz J A, Fisher M J, Heidary G, Dombi E, Packer R J, et al. Orbital/Peri-Orbital Plexiform Neurofibromas in Children with Neurofibromatosis type 1: Multi-disciplinary Recommendations for Care. Ophthalmology. 2017; 124:123-32.
6. Farid M, Demicco E G, Garcia R, Ahn L, Merola P R, Cioffi A, et al. Malignant Peripheral Nerve Sheath Tumors. Oncologist. 2014; 19:193-201.
7. Philpott C, Tovell H, Frayling I M, Cooper D N, Upadhyaya M. The NFL somatic mutational landscape in sporadic human cancers. Hum Genomics [Internet]. 2017 [cited 2019 Apr. 1]; 11. Available from: www.ncbi.nlm-.nih.gov/pmc/articles/PMC5480124/
8. Alcantara Llaguno S R, Wang Z, Sun D, Chen J, Xu J, Kim E, et al. Adult Lineage-Restricted CNS Progenitors Specify Distinct Glioblastoma Subtypes. Cancer Cell. 2015; 28:429-40.
9. McGillicuddy L T, Fromm J A, Hollstein P E, Kubek S, Beroukhim R, De Raedt T, et al. Proteasomal and Genetic Inactivation of the NF1 Tumor Suppressor in Gliomagenesis. Cancer Cell. 2009; 16:44-54.
10. Gutmann D H, Ferner R E, Listernick R H, Korf B R, Wolters P L, Johnson K J. Neurofibromatosis type 1. Nature Reviews Disease Primers. 2017; 3:17004.
11. See W L, Tan I-L, Mukherjee J, Nicolaides T, Pieper R O. Sensitivity of Glioblastomas to Clinically Available MEK Inhibitors Is Defined by Neurofibromin 1 Deficiency. Cancer Res. 2012; 72:3350-9.
12. Maertens O, Johnson B, Hollstein P, Frederick D T, Cooper Z A, Messiaen L, et al. Elucidating distinct roles for NF1 in melanomagenesis. Cancer Discov. 2013; 3:338-49.
13. Sabatini D M. mTOR and cancer: insights into a complex relationship. Nature Reviews Cancer. 2006; 6:729-34.
14. Dombi E, Baldwin A, Marcus U, Fisher M J, Weiss B, Kim A, et al. Activity of Selumetinib in Neurofibromatosis Type 1—Related Plexiform Neurofibromas. New England Journal of Medicine. 2016; 375:2550-60.
15. Wood M, Rawe M, Johansson G, Pang S, Soderquist R S, Patel A V, et al. Discovery of a Small Molecule Targeting IRA2 Deletion in Budding Yeast and Neurofibromin Loss in Malignant Peripheral Nerve Sheath Tumor Cells. Mol Cancer Ther. 2011; 10:1740-50.
16. Allaway R J, Wood M D, Downey S L, Bouley S J, Traphagen N A, Wells J D, et al. Exploiting mitochondrial and metabolic homeostasis as a vulnerability in NF1 deficient cells. Oncotarget. 2017; 9:15860-75.
17. Kim H A, Ratner N, Roberts T M, Stiles C D. Schwann Cell Proliferative Responses to cAMP and Nf1 Are Mediated by Cyclin D1. J Neurosci. 2001; 21:1110-6.
18. Emter R, Heese-Peck A, Kralli A. ERG6 and PDRS regulate small lipophilic drug accumulation in yeast cells via distinct mechanisms. FEBS Letters. 2002; 521:57-61.
19. Allen M, Bjerke M, Edlund H, Nelander S, Westermark B. Origin of the U87MG glioma cell line: Good news and bad news. Science Translational Medicine. 2016; 8:354re3-354re3.
20. Sharma A, Singh K Almasan A. Histone H2AX Phosphorylation: A Marker for DNA Damage. In: Bjergbrek L, editor. DNA Repair Protocols [Internet]. Totowa, NJ: Humana Press; 2012 [cited 2019 Apr. 1]. page 613-26. Available from: doi.org/10.1007/978-1-61779-998-3_40
21. Lavrik I N, Golks A, Krammer P H. Caspases: pharmacological manipulation of cell death. J Clin Invest. 2005; 115:2665-72.
22. Liu W J, Ye L, Huang W F, Guo L J, Xu Z G, Wu H L, et al. p62 links the autophagy pathway and the ubiqutin-proteasome system upon ubiquitinated protein degradation. Cellular & Molecular Biology Letters [Internet]. 2016 [cited 2019 Apr. 1]; 21. Available from: cmbl.biomedcentral.com/articles/10.1186/s11658-016-0031-z
23. Chaitanya G V, Alexander J S, Babu P P. PARP-1 cleavage fragments: signatures of cell-death proteases in neurodegeneration. Cell Commun Signal. 2010; 8:31.
24. Verdoes M, Florea B I, Menendez-Benito V, Maynard C J, Witte M D, van der Linden W A, et al. A Fluorescent Broad-Spectrum Proteasome Inhibitor for Labeling Proteasomes In Vitro and In Vivo. Chemistry & Biology. 2006; 13:1217-26.
25. Song C, Mitter S K, Qi X, Beli E, Rao H V, Ding J, et al. Oxidative stress-mediated NFκB phosphorylation upregulates p62/SQSTM1 and promotes retinal pigmented epithelial cell survival through increased autophagy. PLOS ONE. 2017; 12:e0171940.
26. Nedelsky N B, Todd P K, Taylor J P. Autophagy and the ubiquitin-proteasome system: Collaborators in neuroprotection. Biochimica et Biophysica Acta (BBA)-Molecular Basis of Disease. 2008; 1782:691-9.
27. Mauthe M, Orhon I, Rocchi C, Zhou X, Luhr M, Hijlkema K-J, et al. Chloroquine inhibits autophagic flux by decreasing autophagosome-lysosome fusion. Autophagy. 2018; 14:1435-55.
28. Tanida I, Ueno T, Kominami E. LC3 and Autophagy. In: Deretic V, editor. Autophagosome and Phagosome [Internet]. Totowa, NJ: Humana Press; 2008 [cited 2019 Apr. 1]. page 77-88. Available from: doi.org/10.1007/978-1-59745-157-4_4
30. Mizushima N, Yoshimori T. How to Interpret LC3 Immunoblotting. Autophagy. 2007; 3:542-5.
31. Guo J Y, Chen H-Y, Mathew R, Fan J, Strohecker A M, Karsli-Uzunbas G, et al. Activated Ras requires autophagy to maintain oxidative metabolism and tumorigenesis. Genes Dev. 2011; 25:460-70.
32. Valavanidis A, Vlachogianni T, Fiotakis C. 8-hydroxy-2'-deoxyguanosine (8-OHdG): A critical biomarker of oxidative stress and carcinogenesis. J Environ Sci Health C Environ Carcinog Ecotoxicol Rev. 2009; 27:120-39.
33. Mancias J D, Kimmelman A C. Mechanisms of Selective Autophagy in Normal Physiology and Cancer. Journal of Molecular Biology. 2016; 428:1659-80.
34. Hamacher-Brady A, Brady N R. Mitophagy programs: mechanisms and physiological implications of mitochondrial targeting by autophagy. Cell Mol Life Sci. 2016; 73:775-95.
35. Al-Mehdi A-B, Pastukh V M, Swiger B M, Reed D J, Patel M R, Bardwell G C, et al. Perinuclear Mitochondrial Clustering Creates an Oxidant-Rich Nuclear Domain Required for Hypoxia-Induced Transcription. Sci Signal. 2012; 5:ra47.
36. Xu H, Gopalsamy A, Hett E C, Salter S, Aulabaugh A, Kyne R E, et al. Cellular thermal shift and clickable chemical probe assays for the determination of drug-target engagement in live cells. Org Biomol Chem. 2016; 14:6179-83.
37. Jafari R, Almqvist H, Axelsson H, Ignatushchenko M, Lundback T, Nordlund P, et al. The cellular thermal shift assay for evaluating drug target interactions in cells. Nature Protocols. 2014; 9:2100-22.
38. Jung Y-S, Qian Y, Chen X. Examination of the expanding pathways for the regulation of p21 expression and activity. Cellular Signalling. 2010; 22:1003-12.
39. Zhao H, Darzynkiewicz Z. Biomarkers of Cell Senescence Assessed by Imaging Cytometry. Methods Mol Biol. 2013; 965:83-92.
40. Pu J, Schindler C, Jia R, Jarnik M, Backlund P, Bonifacino J S. BORC, a Multisubunit Complex that Regulates Lysosome Positioning. Developmental Cell. 2015; 33:176-88.
41. Pu J, Guardia C M, Keren-Kaplan T, Bonifacino J S. Mechanisms and functions of lysosome positioning. Journal of Cell Science. 2016; 129:4329-39.
42. Pu J, Keren-Kaplan T, Bonifacino J S. A Ragulator-BORC interaction controls lysosome positioning in response to amino acid availability. J Cell Biol. 2017; 216:4183-97.
43. Jia R, Guardia C M, Pu J, Chen Y, Bonifacino J S. BORC coordinates encounter and fusion of lysosomes with autophagosomes. Autophagy. 2017; 13:1648-63.
44. Qiao S, Tao S, Vega M R de la, Park S L, Vonderfecht A A, Jacobs S L, et al. The antimalarial amodiaquine causes autophagic-lysosomal and proliferative blockade sensitizing human melanoma cells to starvation- and chemotherapy-induced cell death. Autophagy. 2013; 9:2087-102.
45. Varin J, Poulain L, Hivelin M, Nusbaum P, Hubas A, Laurendeau I, et al. Dual mTORC1/2 inhibition induces anti-proliferative effect in NF1-associated plexiform neurofibroma and malignant peripheral nerve sheath tumor cells. Oncotarget. 2016; 7:35753-67.
46. Daginakatte G C, Gutmann D H. Neurofibromatosis-1 (Nf1) heterozygous brain microglia elaborate paracrine factors that promote Nf1-deficient astrocyte and glioma growth. Hum Mol Genet. 2007; 16:1098-112.
47. Allaway R J, Fischer D A, Abreu F B de, Gardner T B, Gordon S R, Barth R J, et al. Genomic characterization of patient-derived xenograft models established from fine needle aspirate biopsies of a primary pancreatic ductal adenocarcinoma and from patient-matched metastatic sites. Oncotarget. 2016; 7:17087-102.
48. Eng J K, Jahan T A, Hoopmann M R. Comet: An open-source MS/MS sequence database search tool. PROTEOMICS. 2013; 13:22-4.
49. Franken H, Mathieson T, Childs D, Sweetman G M A, Werner T, Tögel I, et al. Thermal proteome profiling for unbiased identification of direct and indirect drug targets using multiplexed quantitative mass spectrometry. Nature Protocols. 2015; 10:1567-93.
50. Katayama H, Kogure T, Mizushima N, Yoshimori T, Miyawaki A. A sensitive and quantitative technique for detecting autophagic events based on lysosomal delivery. Chemistry and Biology. 2011; 18:1042-52.

We claim:

1. A method for treating or preventing a disorder associated with NF1 deficiency comprising administering to a subject a therapeutically effective amount of a compound Y102_01, or pharmaceutically acceptable salts thereof.

2. The method of claim 1, wherein the disorder associated with NF1 deficiency is selected from the group consisting of glioblastoma, melanoma, breast ovarian and lung cancers.

3. The method of claim 1, wherein the disorder associated with NF1 deficiency is glioblastoma.

* * * * *